(12) United States Patent
Austin-Phillips et al.

(10) Patent No.: US 6,818,803 B1
(45) Date of Patent: Nov. 16, 2004

(54) TRANSGENIC PLANTS AS AN ALTERNATIVE SOURCE OF LIGNOCELLULOSIC-DEGRADING ENZYMES

(75) Inventors: Sandra Austin-Phillips, Madison, WI (US); Richard R. Burgess, Madison, WI (US); Thomas L. German, Hollandale, WI (US); Thomas Ziegelhoffer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/373,272

(22) Filed: Aug. 12, 1999

Related U.S. Application Data

(63) Continuation-in-part of application No. 08/883,495, filed on Jun. 26, 1997, now Pat. No. 5,981,835.

(51) Int. Cl.[7] ............................. C12N 15/82; C12N 5/04

(52) U.S. Cl. ..................... 800/278; 435/69.1; 435/70.1; 435/410; 435/414; 435/468; 435/469; 536/23.1; 536/23.74; 800/284; 800/317.3

(58) Field of Search ................................ 800/278, 284, 800/317.3; 536/23.1, 23.74; 435/69.1, 70.1, 468, 469, 410, 414

(56) References Cited

U.S. PATENT DOCUMENTS

| | | |
|---|---|---|
| 5,275,944 A | 1/1994 | Himmel et al. |
| 5,432,074 A | 7/1995 | Evans et al. |
| 5,457,046 A | 10/1995 | Wöldike et al. |
| 5,529,919 A | 6/1996 | Knowles et al. |
| 5,536,655 A * | 7/1996 | Thomas et al. |
| 5,705,375 A * | 1/1998 | Van Ooyen et al. ...... 435/172.3 |
| 5,981,835 A * | 11/1999 | Austin-Phillips et al. |

FOREIGN PATENT DOCUMENTS

| | | |
|---|---|---|
| EP | 0 449 376 A | 10/1991 |
| EP | 0 479 359 A | 4/1992 |
| GB | 2 046 567 A | 11/1980 |
| WO | WO 87/00865 | 2/1987 |
| WO | 0 311 469 A | 4/1989 |
| WO | WO 91 16440 A | 10/1991 |
| WO | WO 92 01042 A | 1/1992 |
| WO | WO 93 20714 A | 10/1993 |
| WO | WO 94/26880 | 11/1994 |
| WO | WO 94/29460 | 12/1994 |
| WO | WO 96 00281 A | 1/1996 |
| WO | WO 96 04781 A | 2/1996 |
| WO | WO 96 29415 A | 9/1996 |

OTHER PUBLICATIONS

Shiyaron et al. GenBank accession No. E00389. DNA coding for cellobiohydrolase I isolated from *Trichoderma reesei*.*

Adney et al. (1994), Cellulase assays. In: *Enzymatic conversion of biomass for fuels production*, Eds. M. E. Himmel, J.O. Baker & R.P. Overend. ACS symposium series 566.

Aspegren et al. (1995), Secretion of a heat–stable fungal β–glucanase from transgenic, suspension–cultured barley cells. *Molecular Breeding* 1:91–99.

Baker et al. (1992), Thermal denaturation of *T. reesei* cellulases studied by differential scanning calorimetry and tryptophan fluorescence. *Apply. Biochem. Biophys.* 34:217–231.

Bednarek (1991), The barley lectin carboxy–terminal peptide is a vacuolar protein sorting determinant in plants. *The Plant Cell* 3:1195–1206.

Belkacemi et al. (1996), Enzymatic hydrolysis of timothy grass pretreated by ammonia fiber explosion. In: *Liquid fuels and industrial products from renewable resources, Proceedings of the third liquid fuel conference*, Eds. J.S. Cundiff, E.E. Gavett, C. Hansen, C. Peterson, M.A. Sanderson, H. Shapouri & D.L. VanDyne. ASAE publication 08–96 pp 232–240.

Bingham et al. (1975), Breeding alfalfa which regenerates from callus tissue in culture. *Crop Sci.* 15:719–721.

Brown and Atanassov (1985), Role of genetic background in somatic embryogenesis in Medicago. *Plant Cell Tissue Organ Culture* 4:107–114.

Carrer et al. (1993), Kanamycin resistance as a selectable marker for plastid transformation in tobacco. *Mol. Gen. Genet.* 241:49–56.

Castillo et al. (1994), Rapid production of fertile transgenic plants of Rye. *Bio/Technology* 12:1366–1371.

Cheng et al. (1990), *Nucleic Acids Res.*, 18:5559.

Comai et al. (1990), Novel and useful properties of a chimeric plant promoter combining CaMV 35S and MAS elements. *Plant Mol. Biol.* 15:373–381.

Coughlin, M.P. (1988), Staining Techniques for the Detection of the Individual Components of Cellulolytic Enzyme Systems. *Methods in Enzymology* 160:135–144.

*Current Protocols in Molecular Biology*, vols. 103, Series Editor, Virginia Benson Changa. ©1987–1997, John Wiley & Sons, Inc.

de Castro Silva Filho et al. (1996), Mitochondrial and chloroplast targeting sequences in tandem modify protein import specificity in plant organelles. *Plant Mol. Biol.* 30:769–780.

Divne et al. (1994), The three–dimensional crystal structure of the catalytic core of cellobiohydrolase I from *Trichoderma reesei*. *Science* 265:524–528.

(List continued on next page.)

Primary Examiner—Janet L. Epps-Ford
(74) Attorney, Agent, or Firm—Joseph T. Leone, Esq.; DeWitt Ross & Stevens S.C.

(57) ABSTRACT

Transgenic plants which express cellulose-degrading enzymes, methods to make the transgenic plants, and methods to use the cellulose-degrading enzymes produced by the transgenic plants are disclosed.

12 Claims, 12 Drawing Sheets

OTHER PUBLICATIONS

Ghangas & Wilson (1988), Cloning of the *Thermomonospora fusca* endoglucanase E2 gene in *Streptomyces lividans*: Affinity purification and functional domains of the cloned gene product. *Appl. Envir. Microbiol.* 54:2521–2526.

Grohmann et al. (1992), Potential for fuels from biomass and wastes. In: *Emerging technologies for materials and chemicals from biomass*, Eds. R.M. Powell, T.P. Schultz and R. Narayan. ACS Symposium series 576.

Henrissat et al. (1995), Synergism of cellulases from *Trichoderma reesei* in the degradation of cellulose. *Bio/Technology* 3:722–726.

Herbers, K. et al., A Thermostable Xylanase from *Clostridium thermocellum* Expressed at High Levels in the Apoplast of Transgenic Tobacco Has No Detrimental Effects and Is Easily Purified, *Bio/Technology* (1995), 13:1:63–66.

Horsh et al. (1985), A simple and general method for transferring genes into plants. Science 227:1229–1231.

Irwin et al. (1993), Activity studies of eight purified cellulases: Specificity, synergism, and binding domain effects. *Biotechnol. Bioeng.* 42:1002–1013.

Irwin et al. (1999), Characterization of a *Thermomonospora fusca* family 48 exocellulase E6. Direct Genbank Submission AF144563.

Ishida et al. (1996), High efficiency transformation of maize mediated by *Agrobacterium tumefaciens*. *Nature Biotechnology* 14:745–750.

Joliff et al. (1986), Nucleotide Sequence of the cellulose gene celD encoding endoglucanase D of *Clostridium thermocellum*, *Nucleic Acids Res.*, 14:8605–8613.

Keegstra et al. (1993), Targeting of proteins into chloroplasts. *Physiologia Plantarum* 93:157–162.

Lao et al., Thermomonospora fusca YX beta–1,4–endoglucanase, complets cds., EMBL Sequence Database Accession No. M73321 (Jul. 17, 1991) (do not have copy of article, but it was cited in foreign communication).

Lao et al., DNA sequences of three beta–1,4–endoglucanase genes from *Thermomonospora fusca*, *J. Bacteriol.* (1991), 173:3397–3407 (do not have copy of article, but it was cited in a foreign communication).

Lin, E.S. et al., Identification of a celE–binding protein and its potential role in induction of the celE gene in *Termomonospora fusca*, J. Bacteriology (1988), 170:3843–3846.

Liu and Doi (1998), Properties of exgS a gene for a major subunit of the *Clostridium cellolovorans* cellulosome, Gene 211:39–47.

Mason et al. (1988), Proteins homologous to leaf glycoproteins are abundant in stems of dark–grown soy bean seedlings. Analysis of proteins in cDNAs. *Plant Mol. Biol.* 11:845–856.

McBride and Summerfelt (1990), Improved binary vectors for *Agrobacterium* mediated plant transformation. *Plant Mol. Biol.* 14:269–276.

McBride et al. (1994), Controlled expression of plastid transgenes in plants based on a nuclear DNA–encoded and plastid–targeted T7 RNA polymerase. *Proc. Natl. Acad. Sci. USA* 91:7301–7305.

Micelli et al. (1996), Integrated treatments of steam explosion and enzymatic hydrolysis to produce energetic and industrial products from lignocellulosic biomasses. *Agro–food–Industry Hi–tech* 7:25–28.

Murashige and Skoog (1962), A revised medium for rapid growth and bioassays with tobacco tissue cultures. *Physiol. Plant* 15:473–497.

Pen et al., Production of Active Bacillus Licheniformis Alpha–Amylase in Tobacco and Its Application in Starch Licuefaction, Bio/Techology (1992), 10:3:292–296. Pentilla et al. (1987), *Yeast* 3:175–185.

Shoemaker et al. (1983), Bio. Technology 1:691–696.

Sonnewald et. al. (1991), Transgenic tobacco plants expressing yeast–derived invertase in either the cytosol, vacuole or apoplast: a powerful tool for studying sucrose metabolism and sink/source interactions. *The Plant J.* 1:95–106.

Spezio et al. (1993), Crystal structure of the catalytic domain of a thermophilic endocellulase. *Biochemistry* 32:9906–9916.

Tucker et al. (1989), Ultra–thermostable cellulases from *Acidothermus cellulolyticus* comparison of temperature optima with previously reported cellulases. *Biotechnology* 7:817–820.

Vasil et al. (1993), Rapid production of transgenic wheat plants by direct particle bombardment of cultured immature embryos. *Bio/Technology* 11:1553–1558.

Wandelt et al. (1992), Vicilin with carboxy–terminal KDEL is retained in the endoplasmic reticulum and accumulates to high levels in the leaves of transgenic plants. *Plant J.* 2:181–192.

Wong et al. (1986) Characterization of an endoglucanase gene cenA of *Cellulomonas fimi.*, Gene 44:315–324.

Zambryski, P., J. Tempe, and J. Schell (1989), Transfer and function of T–DNA genes from *Agrobacterium Ti* and *Ri* plasmids in plants. *Cell* 56:193–201.

Zhang et al. (1995), Characterization of a *Thermomonospora fusca* exocellulase. *Biochemistry* 34:3386–3395.

* cited by examiner

US 6,818,803 B1

TRANSGENIC PLANTS AS AN ALTERNATIVE SOURCE OF LIGNOCELLULOSIC-DEGRADING ENZYMES

This is a continuation-in-part of application Ser. No. 08/883,495, filed Jun. 26, 1997 now U.S. Pat. No. 5,981,835.

This invention was made with United States government support awarded by the following agencies: DOE Grant No. DE-FC05-92OR22072 and USDA Grant Nos. 94-34190-1204 and 92-34190-6941. The United States has certain rights in this invention.

FIELD OF THE INVENTION

The present invention is directed to the production of cellulose-degrading enzymes in genetically recombinant plants and the recombinant plants themselves.

BIBLIOGRAPHY

Complete bibliographic citations for the non-patent references discussed hereinbelow are included in the Bibliography section, immediately preceding the claims. All of the references cited below are incorporated herein by reference.

DESCRIPTION OF THE PRIOR ART

Lignocellulosic plant matter, such as agricultural and forestry waste, as well as energy crops produced specifically for biomass, offer tremendous potential for the renewable production of fuel and as chemical feedstocks. However, production cost for desired products such as alcohols from lignocellulosic material is significantly higher than the production cost of equivalent alternatives. However, the prospect, either real or perceived, of limited fossil fuel reserves, along with the geo-political issues which swirl about petroleum-producing countries and regions, renders the production of basic chemical feedstocks and fuels from local, renewable sources an attractive alternative to fossil fuels.

For instance, alcohols have the potential to be excellent alternative transportation fuels if their production costs can be lowered. Brazil has sponsored several programs to replace car engines which run on gasoline alone to engines which run on ethanol or a gasoline-ethanol mix.

Unfortunately, the production of ethanol and other feedstock chemicals from lignocellulosic material is far more complex than an analogous production utilizing a starch-based starting material. Compared to lignocellulosic materials, starch is a simple polymer which is readily hydrolyzed to glucose. Yeasts can then be used to convert the glucose to ethanol.

In contrast, lignocellulosic biomass is a much more complex substrate in which crystalline cellulose is embedded within a matrix of hemicellulose and lignin. The intricate structure and relative inaccessibility of these substrates requires pre-treatment for the disruption of the lignocellulosic material, as well as hydrolysis of hemicellulose and lignin into xylose and phenolic compounds, respectively. (See, for instance, Micelli et al. (1996), Belkacemi et al. (1996), and Grohmann et al. (1992).)

Several enzymes which degrade lignocellulosic material, commonly referred to as "cellulases," are known. The term "cellulase" shall be used herein to refer to any and all enzymes which catalyze the cleavage of cellulosic or lignocellulosic materials. Explicitly, but not exclusively, included within this definition are those cellulases which fall under the Enzyme Classification heading EC 3.2.1.x. Various genes encoding cellulases have also been isolated and characterized.

For instance, genes which encode endoglucanases from the fungus *Trichoderma reesei* are known and have been successfully incorporated and expressed in yeast. See, for instance, Pentilla et al. (1987). Likewise, cellulase E2 (EC 3.2.1.4) and cellulase E3 (EC 3.2.1.91) from the thermotolerant bacterium *Thermomonospora fusca* are known. See Lao et al. (1991), Spezio et al. (1993) and Zhang et al. (1995).

From a functional viewpoint, cellulases are catagorized into two large sub-groups based upon whether they catalyze cleavage from the cellulose chain ends (exocellulases) or if they catalyze cleavage in the middle of the cellulose chain (endocellulases). For instance, cellobiohydrolase I of *T. reesei* (CBH I, EC 3.2.1.91) is an exocellulase, which degrades crystalline cellulose by cleavage from the chain ends. By way of further illustration, CBH I is a 68 kDa protein with a two-domain architecture which is shared by many cellulases. In this chemical architecture, a large catalytic domain is joined to a cellulose-binding domain (CBD) through a flexible linker region. See Divne et al. (1994). Similarly, cellulase E3 of *T. fusca* is also an exocellulase.

Different types of cellulases exhibit synergistic activity on complex substrates. This synergism, especially between exocellulases, is believed to be due to differences in their patterns of absorption to and hydrolysis of complex cellulose substrates. See Henrissat et al. (1995).

Illustratively, cellulase E2 of *T. fusca* is a 40 kDa endocellulase which cleaves the cellulose chain internally. Such cleavage generates more chain ends for attack by exocellulases. Consequently when CBH I, E2, and E3 cellulases are combined, their activity together is approximately 5-fold greater than their additive individual activities. (See, for instance, Irwin et al. (1993) and WO 94/26880.) It is important to note that proteolytic fragments of cellulases can substitute for the intact enzymes in synergistic mixtures. For example, when combined with *T. fusca* E3 and CBH I, the catalytic domain of *T. fusca* E2 ("E2cd") is as active as the intact enzyme in the digestion of filter paper substrate, Irwin et al. (1993).

A wide range of compositions containing cellulases are described in the patent literature. For instance, Evans et al., U.S. Pat. No. 5,432,074, describe the use of a formulation consisting essentially of a combination of xylanase and xylosidase, but being essentially free of glucanase and cellobiohydrolase. The formulation also contains a lactic acid-producing bacteria. The formulation is used to treat silage to increase its nutritive value. In operation, the action of the xylanase and xylosidase enzymes degrades non-cellulosic polysaccharides found in the silage material thereby producing sugars for fermentation.

Heterodimers of different types of cellulose-degrading enzymes are described in WO 94/29460. Here, a β-glucosidase molecule and a cellobiohydrolase molecule (i.e., an exocellulase) are chemically bonded to one another by a crosslinking reagent to yield a single molecule which retains the enzymatic activities of the two separate molecules.

Expression constructs which contain cellulase genes for the transformation of yeast have been constructed. For example, Knowles et al., U.S. Pat. No. 5,529,919, describe the transformation of *S. cerevisiae* to contain and express a thermostable β-endoglucanase (EG I) of *T. reesei*.

Likewise, attempts have been made to produce transgenic plants which express cellulose-degrading enzymes. Aspegren et al. (1995) describe transgenic suspension-cultured barley cells which express EG I of *T. reesei*. The cells were transformed by particle bombardment and transformed cells selected by a co-transformed antibiotic resistance marker. However, no attempt was made to regenerate complete plants from the cultured cells. Of particular note, this reference states that the production of β-glucanases in plant cells may be hampered by the fact that these enzymes catalyze the hydrolysis of essential cell wall components. Attempts by these authors to stably transform tobacco cells with the same construct used to successfully transform the suspended barley cells failed. Here, the authors observed that after transient expression in tobacco protoplasts, cell wall synthesis never resumed.

SUMMARY OF THE INVENTION

The present invention is drawn to genetically recombinant plants which contain one or more exogenous gene sequences which encode one or more cellulose-degrading gene products. The gene product or products are expressed in recoverable quantities in the recombinant plants and can be isolated from the plants, if desired. In the preferred embodiment, the genetically recombinant plant expresses the gene product constituitively.

However, the invention also encompasses recombinant plants which express the gene product stage-specifically or tissue-specifically. For example, the gene product or products can be expressed in a plant tissue such as the seeds, fruit, leaves, or tubers of the transformed plant host.

The invention is further drawn to recombinant plants as noted above, wherein the plant contains two exogenous genes whose respective gene products are expressed independently of one another. This allows for different types of cellulases to be expressed in different locations within the same recombinant plant. For example, the plant host can be transformed to express two or more heterologous cellulases in different sub-cellular compartments such as the plastid, cytosol, endoplasmic reticulum, mitochondrion, inclusion body, or vacuole. In addition, chloroplast targeting can also be accomplished through the use of direct chloroplast transformation, an approach that circumvents many of the problems associated with expression of heterologous genes in the nuclear genome. Carrer et al. (1993), McBride et al. (1994).

The invention is further drawn to a method for producing cellulose-degrading enzymes. The method comprises transforming a plant host with one or more exogenous genes which encode one or more cellulose-degrading gene products such that the gene product or products are expressed in recoverable quantities. The plant matter containing the expressed protein can be used directly as a feedstock for biomass conversion, or, if desired, the exogenous enzymes so produced can be isolated and purified.

The cellulases produced by the transgenic plants of the present invention can be utilized in the same manner as conventionally-derived cellulases. For instance, cellulases produced by the transgenic plants of the present invention can be isolated and used in fermentation processes such as brewing and wine-making. Here, the cellulases function to hydrolyze cellulose and β-glucans during fermentation. Or, as described in Example 4, below, whole plants transformed to express cellulases can be used directly or added to ensiled plant matter to increase the extent of fermentation of the ensiled matter. Plants transformed to express functional cellulases may also be fed directly to livestock, where the cellulase activity aids in the digestion of lignocellulosic substrates.

Cellulases produced in the transgenic plants of the present invention can also be utilized in the production of ethanol and other feedstock chemicals from lignocellulosic substrates.

Cellulases produced by transgenic plants of the present invention can also be used in the textile, pulping, and paper-making industries. For instance, cellulases are conventionally used to treat denim fabrics to give them a "stone-washed" appearance. Cellulases are also used to modify paper pulps by digesting the cellulose fibers contained within the pulp. The cellulases produced by the transgenic plants described herein can be used in this fashion.

Figure 8:
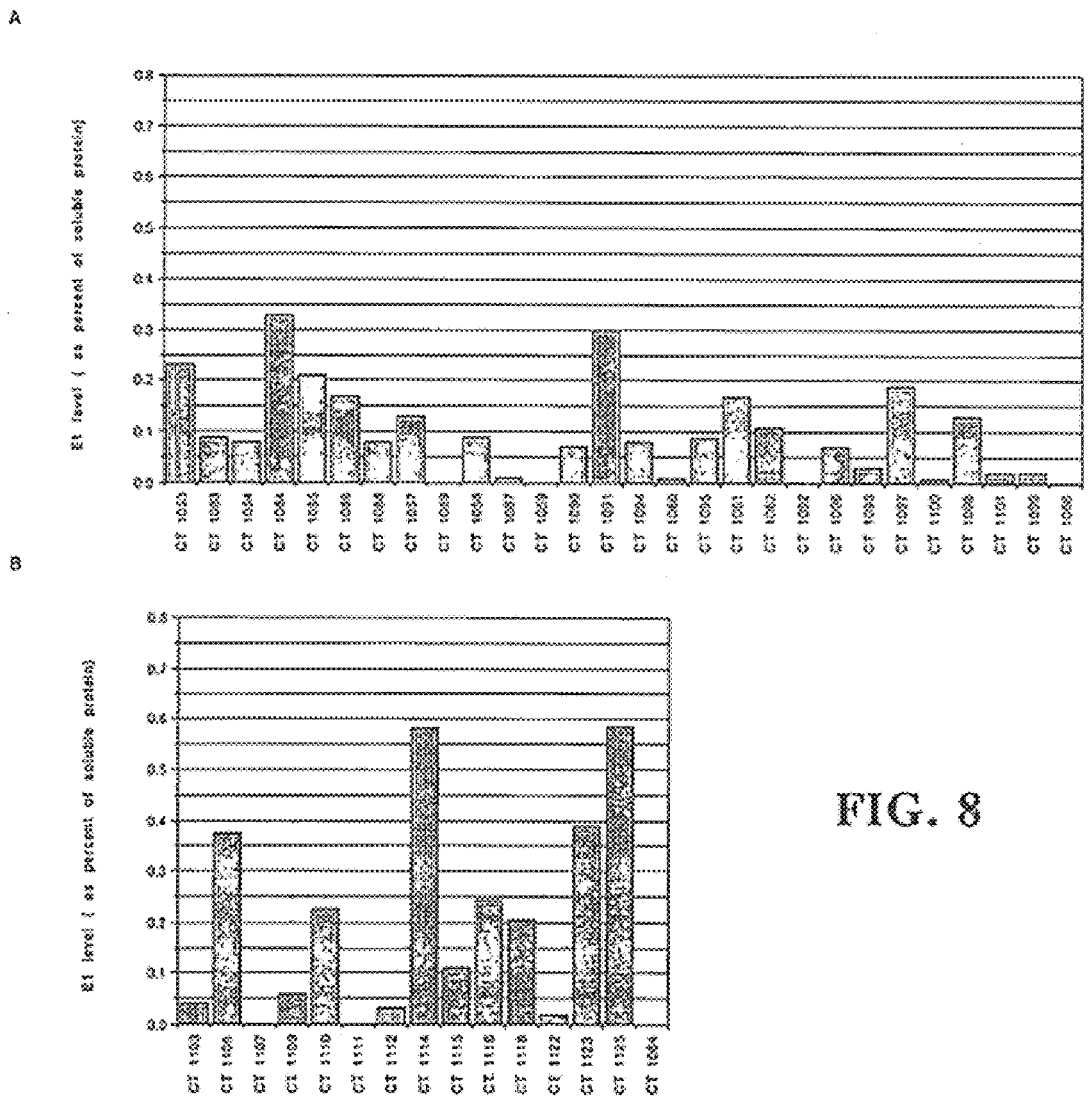
FIG. 8A is a plot of data from an activity assay evidencing the expression of *A. cellulolyticus* E1 cellulase in tobacco transformed with Agrobacterium strain PZA8.

At FIG. 8B is a plot of data from an activity assay evidencing the expression of *A. cellulolyticus* E1 cellulase in tobacco transformed with Agrobacterium strain PZA9.

Figure 9:
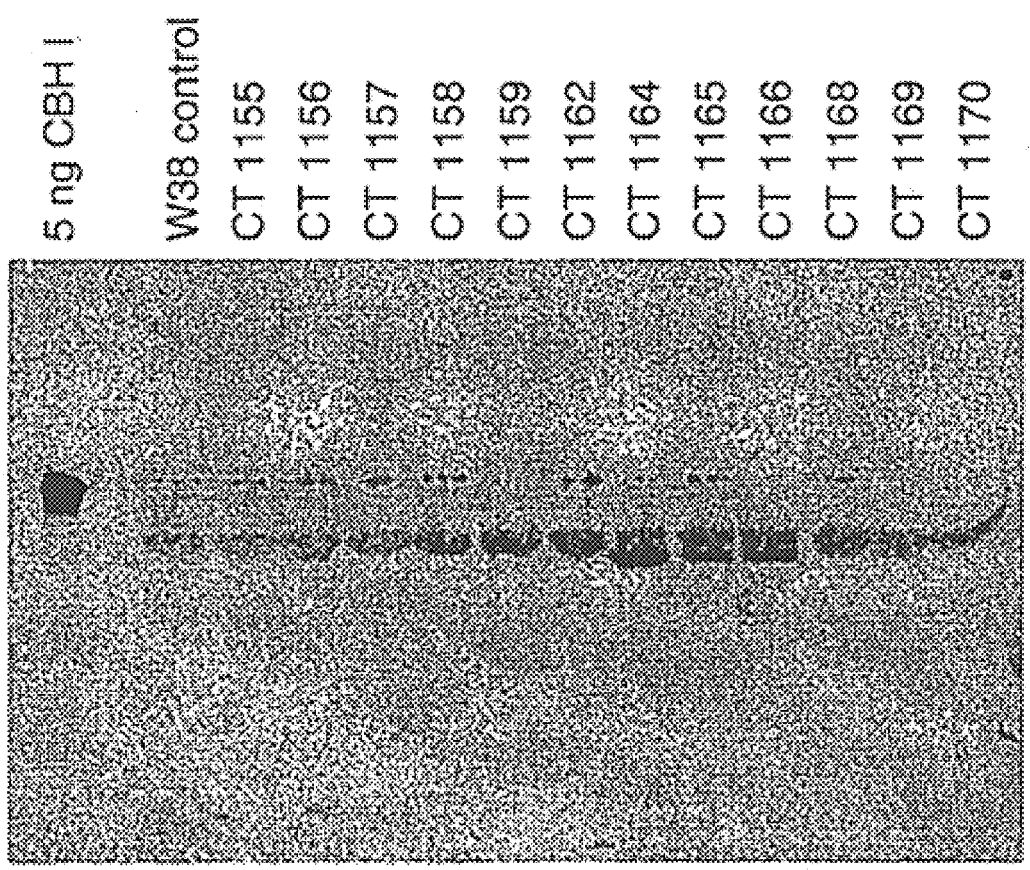

FIG. 9 is a western blot analysis evidencing the expression of CBH I cellulase of *T. Reesei* in tobacco transformed to contain the expression construct depicted in FIG. 7.

Figure 10:
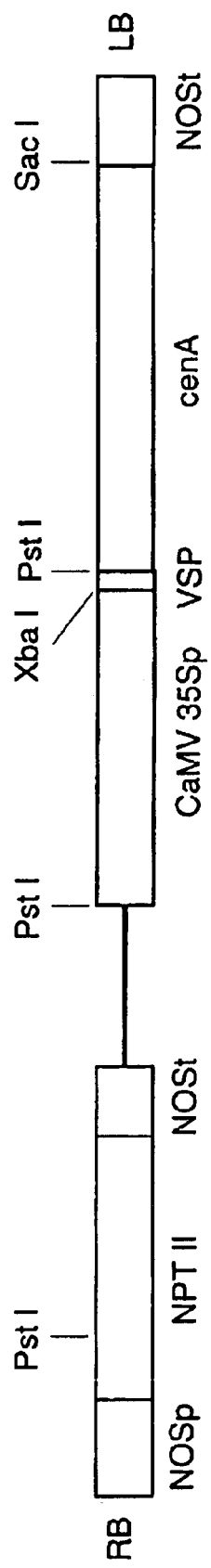

FIG. 10 is a schematic diagram of binary vector T-DNA for an expression construct to transform plants to contain the CenA endoglucanase of *Cellulomonas fimi*.

Figure 11:
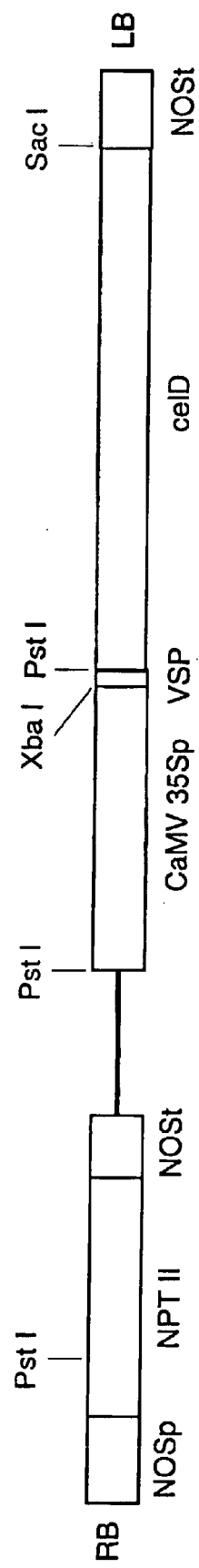

FIG. 11 is a schematic diagram of binary vector T-DNA for an expression construct to transform plants to contain endoglucanase D of *Clostridium thermocellum*.

Figure 12:
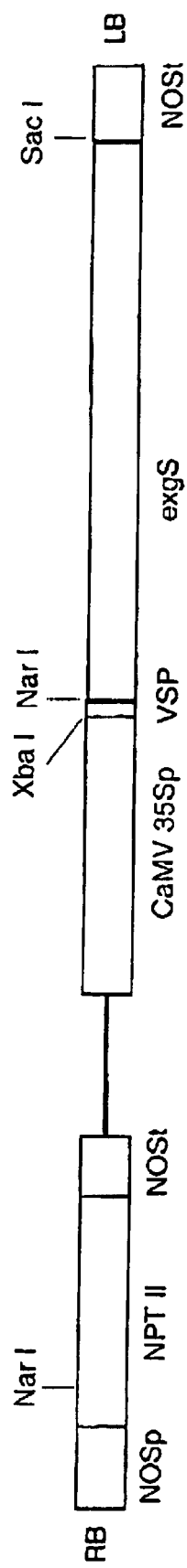

FIG. 12 is a schematic diagram of binary vector T-DNA for an expression construct to transform plants to contain exoglucanase S of *Clostridium cellulovorans*.

Figure 13:
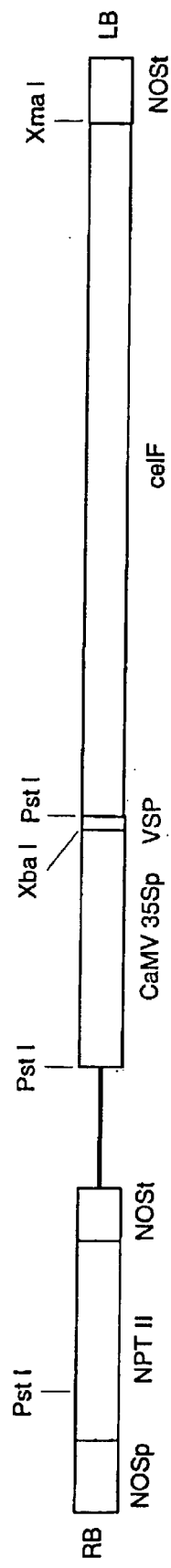

FIG. 13 is a schematic diagram of binary vector T-DNA for an expression construct to transform plants to contain exocellulase E6 of *Thermobifida fusca*.

DETAILED DESCRIPTION OF THE INVENTION

The invention is directed to genetically recombinant plants which express one or more exogenous cellulose-degrading (cellulase) enzymes. The invention is further drawn to a method of producing cellulases in plants. The invention allows the production of cellulases using the means and methods of large-scale agriculture rather than the conventional route of large-scale fermentation of the bacteria or fungi which are native producers of the cellulases.

The recombinant plants are produced by incorporating into a plant host genome one or more expression constructs comprising a DNA sequence which encodes a protein having cellulose-degrading activity. Introduction of the exogenous gene or genes into the plant is accomplished by any means known to the art. The expression constructs described hereinbelow enable the stable transformation of plants with one or more genes which encode cellulose-degrading enzymes. The constructs include a DNA coding sequence which encodes a cellulase (as that term is described herein) which is operatively linked to regulatory sequences which direct constituitive, stage-specific, or tissue-specific expression of the cellulase DNA.

Cellulose-Degrading Enzymes (Cellulases) and Genes:

As noted above, the term "cellulase" shall be used herein to refer to any and all enzymes which catalyze the cleavage of cellulosic or lignocellulosic materials. As used herein, "cellulase" is synonymous with "cellulose-degrading enzymes." Explicitly, but not exclusively, included within the term cellulases are those enzymes which fall under the Enzyme Classification heading EC 3.2.1.x. A non-exhaustive list of these enzymes, the genes for all of which can be used in the present invention, includes the following:

TABLE 1

Polysaccharide-Degrading Enzymes

EC 3.2.1.1 (Alpha-amylase)
EC 3.2.1.2 (Beta-amylase)
EC 3.2.1.3 (Glucan 1,4-alpha-glucosidase)
EC 3.2.1.4 (Cellulase, also known as beta-1,4-endoglucanase, e.g., cellulase E2)
EC 3.2.1.6 (Endo-1,3(4)-beta-glucanase)
EC 3.2.1.7 (Inulinase)
EC 3.2.1.8 (Endo-1,4-beta-xylanase)
EC 3.2.1.10 (Oligo-1,6-glucosidase)
EC 3.2.1.11 (Dextranase)
EC 3.2.1.14 (Chitinase)
EC 3.2.1.15 (Polygalacturonase)
EC 3.2.1.17 (Lysozyme)
EC 3.2.1.18 (Exo-alpha-sialidase)
EC 3.2.1.20 (Alpha-glucosidase)
EC 3.2.1.21 (Beta-glucosidase)
EC 3.2.1.22 (Alpha-galactosidase)
EC 3.2.1.23 (Beta-galactosidase)
EC 3.2.1.24 (Alpha-mannosidase)
EC 3.2.1.25 (Beta-mannosidase)
EC 3.2.1.26 (Beta-fructofuranosidase)
EC 3.2.1.28 (Alpha,alpha-trehalase)
EC 3.2.1.31 (Beta-glucuronidase)
EC 3.2.1.32 (Xylan endo-1,3-beta-xylosidase)
EC 3.2.1.33 (Amylo-1,6-glucosidase)

TABLE 1-continued

Polysaccharide-Degrading Enzymes

EC 3.2.1.35 (Hyaluronoglucosminidase)
EC 3.2.1.36 (Hyaluronoglucuronidase)
EC 3.2.1.37 (Xylan 1,4-beta-xylosidase)
EC 3.2.1.38 (Beta-D-fucosidase)
EC 3.2.1.39 (Glucan endo-1,3-beta-D-glucosidase)
EC 3.2.1.40 (Alpha-1-rhamnosidase)
EC 3.2.1.41 (Alpha-dextrin endo-1,6-alpha-glucosidase)
EC 3.2.1.42 (GDP-glucosidase)
EC 3.2.1.43 (Beta-L-rhamnosidase)
EC 3.2.1.44 (Fucoidanase)
EC 3.2.1.45 (Glucosylceramidase)
EC 3.2.1.46 (Galactosylceramidase)
EC 3.2.1.47 (Galactosylgalactosylglucosylceramidase)
EC 3.2.1.48 (Sucrose alpha-glucosidase)
EC 3.2.1.49 (Alpha-N-acetylgalactosaminidase)
EC 3.2.1.50 (Alpha-N-acetylglucosaminidase)
EC 3.2.1.51 (Alpha-L-fucosidase)
EC 3.2.1.52 (Beta-N-acetythexosaminidase)
EC 3.2.1.53 (Beta-N-acetylgalactosaminidase)
EC 3.2.1.54 (Cyclomaltodextrinase)
EC 3.2.1.55 (Alpha-N-arabinofuranosidase)
EC 3.2.1.56 (Glucuronosyl-disulfoglucosamine glucuronidase)
EC 3.2.1.57 (Isopullulanase)
EC 3.2.1.58 (Glucan 1,3-beta-glucosidase)
EC 3.2.1.59 (Glucan endo-1,3-alpha-glucosidase)
EC 3.2.1.60 (Glucan 1,4-alpha-maltotetrahydrolase)
EC 3.2.1.61 (Mycodextranase)
EC 3.2.1.62 (Glycosylceramidase)
EC 3.2.1.63 (1,2-Alpha-L-fucosidase)
EC 3.2.1.64 (2,6-Beta-fructan 6-levanbiohydrolase)
EC 3.2.1.65 (Levanase)
EC 3.2.1.66 (Quercitrinase)
EC 3.2.1.67 (Galacturan 1,4-alpha-galacturonidase)
EC 3.2.1.68 (Isoamylase)
EC 3.2.1.70 (Glucan 1,6-alpha-glucosidase)
EC 3.2.1.71 (Glucan endo-1,2-beta-glucosidase)
EC 3.2.1.72 (Xylan 1,3-beta-xylosidase)
EC 3.2.1.73 (Licheninase)
EC 3.2.1.74 (Glucan 1,4-beta-glucosidase)
EC 3 2.1.75 (Glucan endo-1,6-beta-glucosidase)
EC 3.2.1.76 (L-iduronidase)
EC 3.2.1.77 (Mannan 1,2-(1 3)-alpha-mannosidase)
EC 3.2.1.78 (Mannan endo-1,4-beta-mannosidase)
EC 3.2.1.80 (Fructan beta-fructosidase)
EC 3.2.1.81 (Agarase)
EC 3.2.I.82 (Exo-poly-alpha-galacturonosidase)
EC 3.2.1.83 (Kappa-carrageenase)
EC 3.2.1.84 (Glucan 1,3-alpha-glucosidase)
EC 3.2.1.85 (6-Phospho-beta-galactosidase)
EC 3.2.1.86 (6-Phospho-beta-glucosidase)
EC 3.2.1.87 (Capsular-polysaccharide endo-1,3-alpha-galactosidase)
EC 3.2.1.88 (Beta-L-arabinosidase)
EC 3.2.1.89 (Arabinogalactan endo-1,4-beta-galactosidase)
EC 3.2.1.90 (Arabinogalactan endo-1,3-beta-galactosidase)
EC 3.2.1.91 (Cellulose 1,4-beta-cellobiosidase, also known as beta-1,4-exocellulases; cellobiohydrolases; and exoglucanases; e.g., cellulase E3, CBH I)
EC 3.2.1.92 (Peptidoglycan beta-N-acetylmuramidase)
EC 3.2.1.93 (Alpha,alpha-phosphotrehalase)
EC 3.2.1.94 (Glucan 1,6-alpha-isomaltosidase)
EC 3.2.1.95 (Dextran 1,6-alpha-isomaltotriosidase)
EC 3.2.1.96 (Mannosyl-glycoprotein endo-beta-N-acetylglucosamidase)
EC 3.2.1.97 (Glycopeptide alpha-N-acetylgalactosaminidase)
EC 3.2.1.98 (Glucan 1,4-alpha-maltohexaosidase)
EC 3.2.1.99 (Arabinan endo-1,5-alpha-L-arabinosidase)
EC 3.2.1.100 (Mannan 1,4-beta-mannobiosidase)
EC 3.2.1.101 (Mannan endo-1,6-beta-mannosidase)
EC 3.2.1.102 (Blood-group-substance endo-1,4-beta-galactosidase)
EC 3.2.1.103 (Keratan-sulfate endo-1,4-beta-galactosidase)
EC 3.2.1.104 (steryl-beta-glucosidase)
EC 3.2.1.105 (Strictosidin beta-glucosidase)
EC 3.2.1.106 (Mannosyl-oligosaccharide glucosidase)
EC 3.2.1.107 (Protein-glucosylgalactosylhydroxylysine glucosidase)
EC 3.2.1.108 (Lactase)
EC 3.2.1.109 (Endogalactosaminidase)
EC 3.2.1.111 (Mucinaminylserine mucinaminidase)
EC 3.2.1.111 (1,3-Alpha-L-fucosidase)

TABLE 1-continued

Polysaccharide-Degrading Enzymes

EC 3.2.1.112 (Deoxglucosidase)
EC 3.2.1.113 (Mannosyl-oligosaccharide 1,2-alpha-mannosidase)
EC 3.2.1.114 (Mannosyl-oligosaccharide 1,3-1,6-alpha-mannosidase)
EC 3.2.1.115 (Branched-dextran exo-1,2-alpha-glucosidase)
EC 3.2.1.116 (Glucan 1,4-alpha-maltotriohydrolase)
EC 3.2.1.117 (Amygdalin beta-glucosidase)
EC 3.2.1.118 (Prunasin beta-glucosidase)
EC 3.2.1.119 (Vicianin beta-glucosidase)
EC 3.2.1.120 (Oligoxyloglucan beta-glycosidase)
EC 3.2.1.121 (Polymannuronate hydrolase)
EC 3.2.1.122 (Maltose-6'-phosphate glucosidase)
EC 3.2.1.123 (Endoglycosylceramidase)
EC 3.2.1.124 (3-Deoxy-2-octulosonidase)
EC 3.2.1.125 (Raucaffricine beta-glucosidase)
EC 3.2.1.126 (Coniferin beta-glucosidase)
EC 3.2.1.122 (1,6-Alpha-L-fucosidase)
EC 3.2.1.128 (Glycyrrhizinate beta-glucuroniidase)
EC 3.2.1- 129 (Endo-alpha-sialidase)
EC 3.2.1.130 (Glycoprotein endo-alpha-1,2-mannosidase)
EC 3.2.1.131 (Xylan alpha-1,2-glucuronosidase)
EC 3.2.1.132 (Chitosanase)
EC 3.2.1.133 (Glucan 1,4-alpha-maltohydrolase)
EC 3.2.1.134 (Difructose-anhydride synthase)
EC 3.2.1.135 (Neopullulanase)
EC 3.2.1.136 (Glucuronoarabinoxylan endo-1,4-beta-xylanase)
EC 3.2.1.137 (Mannan exo-1,2-1,6-alpha-mannosidase)
EC 3.2.1.138 (Anhydrosialidase)

DNA sequences encoding enzymes having any of the above-described functionalities can be obtained from several microbial sources, including bacterial and fungal sources. Cloning the gene or cDNA sequence of the desired enzyme can be achieved by several well-known methods. A preferred method is to purify the cellulase of interest (or purchase a sample if commercially available) and determine its N-terminal amino acid sequence, as well as several internal amino acid sequences, using known methods. Oligonucleotide probes corresponding to the amino acid sequence are then constructed (again using known methods) and used to screen a genomic or cDNA library of the organism from which the cellulase was isolated. Positive hybrids are identified, characterized using known methods (restriction enzyme analysis, etc.), and cloned by known means to yield DNA fragments containing the coding sequence for the desired cellulase activity. (See, for instance, *Current Protocols in Molecular Biology*, Chapters 5 and 6.)

If a partial nucleotide sequence of the cellulase of choice is already known, this information can be used to construct suitable primers to directly clone the corresponding cDNA using the polymerase chain reaction (PCR). (See *Current Protocols in Molecular Biology*, Chapter 15.)

Particularly preferred for use in the present invention are those enzymes falling within the classifications EC 3.2.1.4; EC 3.2.1.6; EC 3.2.1.21; and EC 3.2.1.91. The functionality of these particular enzymes is summarized as follows:

EC 3.2.1.4 enzymes (β-1,4-endoglucanases) hydrolyze internal 1,4 glycosidic bonds of the polysaccharide chain, thereby yielding new chain ends at the surface of cellulose crystals.

EC 3.2.1.6 enzymes (β-1,3-endoglucanases) hydrolyze internal 1,3 glycosidic bonds of the polysaccharide chain, which also results in the formation of new chain ends at the surface of cellulose crystals.

EC 3.2.1.21 enzymes (β-glucosidases) hydrolyze cellobiose into glucose, a readily fermentable substrate.

EC 3.2.1.91 enzymes (β-1,4-exocellulases) cleave cellobiosyl residues (cellobiose is a glucose dimer) from the chain ends of cellulose.

Particularly preferred enzymes (and hence particularly preferred genes) for use in the present invention are cellulase E2 and cellulase E3 of *T. fusca* and CBH I of *T. reesei*.

Expression Constructs:

Once the protein coding sequence (i.e., the cellulase gene) has been identified and isolated, it must be inserted into an appropriate expression construct containing regulatory elements to direct the expression of the gene and to direct secretion of the gene product or targeting of the gene product to a particular sub-cellular location or organelle. Manipulation of oligonucleotide sequences using restriction endonucleases to cleave DNA molecules into fragments and DNA ligase enzymes to unite compatible fragments into a single DNA molecule with subsequent incorporation into a suitable plasmid, cosmid, or other transformation vector are well-known to the art.

A transcription regulatory sequence must be included in the expression construct in order to direct the transformed plant cells to transcribe the inserted cellulase coding sequence. Transcriptional regulators may be inducible or constituitive. Inducible transcription regulators direct transcription of the downstream coding sequences in a tissue-specific or growth-stage specific manner. Constituitive regulators provide for sustained transcription in all cell tissues. For purposes of the present invention, constructs which provide constituitive expression of the coding sequence are preferred.

It is also preferred that the expression construct contain a transcription initiation sequence from the tumor-inducing plasmid (Ti) of Agrobacterium. Several T-DNA transcription initiation sequences are well known and include, without limitation, the octopine synthase, nopaline synthase, and mannopine synthase initiators.

Downstream of the initiation sequence and fused to the coding sequence, the expression construct may be manipulated to contain a leader signal sequence which directs the resulting polypeptide to a particular organelle or targets the expressed product for secretion (or to signal post-transcriptional or post-translational modification of the gene product).

Likewise, the expression construct should also include a termination sequence to signal transcription termination.

To facilitate selection of successfully transformed plants, the expression construct should also include one or more selectable markers. The neomycin phosphotransferase gene (NPT II), a well-characterized and widely employed antibiotic resistance selection marker is preferred. This marker provides resistance to kanamycin. A large number of other markers are known and can be used with equal success (e.g., other antibiotic resistance markers, dihydrofolate reductase, luciferase, β-glucuronidase, and the like).

Figure 1:
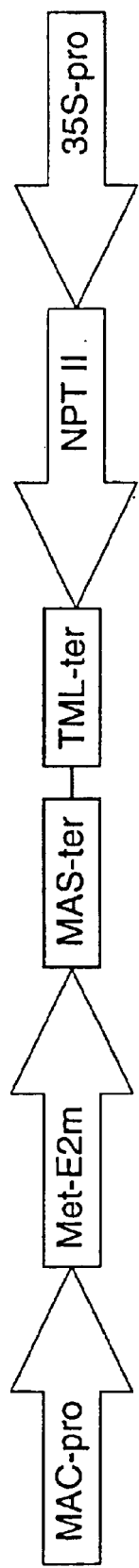
FIG. 1 is a schematic diagram of binary vector T-DNA for an expression construct to transform plants to contain cellulase E2 of *T. fusca*. Promoters and structural genes are depicted as arrows which indicate the direction of transcription. Terminators are depicted as boxes. NPT II=neomycin phosphotransferase; Met-E2m=*T. fusca* E2 (mature form with N-terminal methionine added); MAS-ter=mannopine synthetase terminator; TML-ter=tumor morphology left terminator; MAC-pro=hybrid "MAC" promoter.
Figure 2:
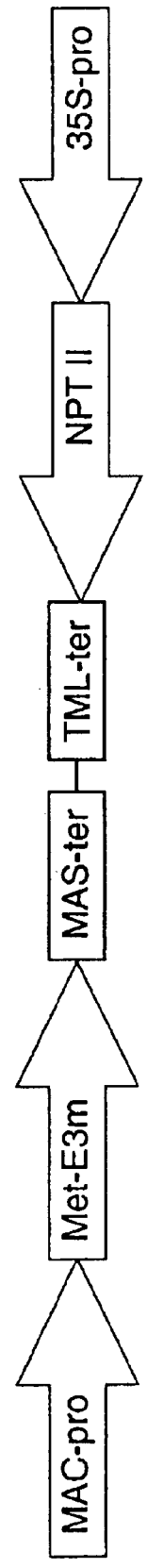
FIG. 2 is a schematic diagram of binary vector T-DNA for an expression construct to transform plants to contain cellulase E3 of *T. fusca*. Promoters and structural genes are depicted as arrows which indicate the direction of transcription. Terminators are depicted as boxes. NPT II=neomycin phosphotransferase; Met-E3m=*T. fusca* E3 (mature form with N-terminal methionine added); MAS-ter=mannopine synthetase terminator; TML-ter=tumor morphology left terminator; MAC-pro=hybrid "MAC" promoter.

For example, FIGS. 1 and 2 depict schematic representations of suitable expression constructs for transformation of plants. These constructs are intended for use with Agrobacterium-mediated transformation using the binary vector approach. However, these same constructs can be coated onto micro-projectiles for transformation by particle bombardment. With the exception of the coding sequence, these two constructs are essentially identical: FIG. 1 is a schematic diagram of binary vector T-DNA for an expression construct to transform plants to contain cellulase E2 of *T. fusca*.

FIG. 2 is a schematic diagram of binary vector T-DNA for an expression construct to transform plants to contain cellulase E3 of *T. fusca*.

In both FIG. 1 and FIG. 2, promoters and structural genes are depicted as arrows which indicate the direction of transcription and terminators are depicted as boxes. See the "Brief Description of the Figures" for a legend to the abbreviations. In the expression constructs depicted in FIGS. 1 and 2, the "MAC" hybrid promoter drives the transcription of the recombinant cellulase genes. Both constructs also contain a constituitive NPT II expression cassette to allow for antibiotic resistance selection using kanamycin. The coding sequence of the construct shown in FIG. 1 (Met-E2m) encodes cellulase E2 from *T. fusca*. (See SEQ. ID. NO: 1; ATG start codon at nt's 255–257, TGA stop codon at nt's 1578–80, first codon of mature E2 protein (AAT) at nt's 348–350.) This sequence encodes the mature form of the enzyme with an N-terminal methionine added. In the same fashion, the coding sequence of the construct shown in FIG. 2 (Met-E3 m) encodes cellulase E3 from *T. fusca*. (See SEQ. ID. NO: 2; ATG start codon at nt's 575–577, TAA stop codon at nt's 2363–65, first codon of mature E3 protein (GCC) at nt's 689–692.) This sequence also encodes the mature form of the enzyme with an N-terminal methionine added.

Further examples of constructs which drive targetted expression of cellulose-degrading enzymes are provided in the Examples hereinbelow. Specifically included in the Examples are transformations illustrating apoplastic targeting and accumulation of two additional cellulases. The first of these is the endoglucanase E1 of *Acidothermus cellulolyticus* (EC 3.2.1.4, SEQ. ID. NO: 8). Also included is the cellobiohydrolase CBH I of *T. Reesei* (EC 3.2.1.91, SEQ. ID. NO: 9). In addition, further Examples of plant expression constructs containing cellulase genes encoding both endoglucanases and cellobiohydrolases (exoglucanase, exocellulase) are provided.

Transformation of Plants:

Transformation of the plants can be accomplished by any means known to the art, including Agrobacterium-mediated transformation, particle bombardment, electroporation, and virus-mediated transformation. The method of transformation is not critical to the functionality of the present invention insofar as the method chosen successfully incorporates the oligonucleotide construct containing the cellulase-encoding region and any accompanying regulatory sequences into the plant host. The nature of the plant host to be transformed has some bearing on the preferred transformation protocol. For dicots, Agrobacterium-mediated transformation utilizing protoplasts or leaf disks is most preferred. Although the Examples disclose the use of tobacco and alfalfa as bioreactors for cellulase production, any crop plant, including monocots, can be utilized. Transformation of monocots is typically achieved by particle bombardment of embryogenic cell lines or cultured embryos. See, for instance, Vasil et al. (1993) and Castillo et al. (1994). Recent developments in "super-binary" vectors, however, also allow for the use of Agrobacterium-mediated gene transfer in most of the major cereal crops. See, for instance, Ishida et al. (1996). In this case, the explant source is typically immature embryos.

Agrobacterium-mediated transformation of the plant host using explants is preferred for its relative ease, efficiency, and speed as compared to other methods of plant transformation. For example, disks are punched from the leaves of the plant host and cultured in a suitable medium where they are then exposed to Agrobacterium containing the expression construct and (preferably) a disarmed tumor-inducing (Ti) plasmid. *Agrobacterium tumefaciens* LBA 4404 is the preferred strain for transformation. The preferred binary vector is the pCGN1578 binary vector (McBride and Summerfelt (1990)).

The binary vector transformation method is well known and needs only be briefly described herein. See Zambryski et al. (1989) for a complete review. The Ti plasmid of Agrobacterium contains virulence genes (vir) which encode trans-acting proteins that enable the transfer of a portion of the plasmid (the T-DNA) to a plant cell. The T-DNA portion of the Ti plasmid is flanked by two border regions (the right and left borders) which act as recognition sites for the excision of the T-DNA from the plasmid prior to its transfer to the plant host. Excision of the T-DNA is mediated by the vir genes of the Ti plasmid and involves nicking of the right and left borders of the T-DNA, which frees a single-stranded oligonucleotide fragment. This fragment is then mobilized out of the Agrobacterium and into the plant host target.

In the binary vector method, the T-DNA with its right and left border regions is cloned into *E. coli* in known fashion, and the wild-type genes normally found between the two border regions is excised. The expression construct encoding the cellulase of interest is inserted between the right and left border regions. This construct is designated the "binary plasmid." Construction of the binary plasmid is accomplished utilizing the well-characterized recombinant genetic methods applicable to *E. coli*. Successful transformants are selected utilizing a co-transformed marker appropriate for *E. coli*.

The binary plasmid is then mobilized back into Agrobacterium. This is accomplished by direct transformation procedures well known to those skilled in the art.

The Agrobacterium itself, such as the preferred LBA 4404 strain, is genetically manipulated to contain a Ti plasmid (called the helper plasmid) which lacks the T-DNA and the tumor-inducing regions (i.e., the Ti plasmid is "disarmed") but which still encodes the virulence proteins necessary for DNA transfer. By cooperation between the helper plasmid and the binary plasmid, the length of DNA between the two border regions of the binary plasmid is excised and mobilized into the plant host, where it is incorporated into the plant host genome. The binary method derives its name from the fact that the plasmid containing the expression construct to be transferred is maintained within Agrobacterium as a distinct and independently replicating vector from the Ti plasmid itself.

Selection of successful transformants is accomplished using the co-transformed selection marker discussed above. If the marker is NPT II, selection is accomplished by treatment with kanamycin.

For the present invention, the most preferred plants for transformation are alfalfa and tobacco. However, any plant species will function with comparable success. Included among the plant species which can be utilized in the present invention are cauliflowers, artichokes, apples, bananas, cherries, cucumbers, grapes, lemons, melons, nuts, oranges, peaches, pears, plums, strawberries, tomatoes, cabbages, endive, leeks, lettuce, spinach, arrowroot, beets, carrots, cassava, turnips, radishes, yams, sweet potatoes, beans, peas, soya, wheat, barley, corn, rice, rapeseed, millet, sunflower, oats, tubers, kohlrabi, potatoes, and the like.

The plants to be transformed are preferably common green field plants, such as the preferred alfalfa and tobacco, as well as soya, corn, and the like. Equally preferred are plant hosts which are grown specifically for "biomass energy," such as switchgrass, poplar, and the like. In this instance, the enzymes would not be recovered from the plants. The plants are then transformed and regenerated into whole plants which express fully-functional, cellulose-degrading enzymes in economically significant quantities. Alfalfa is one of the most preferred plant species for use in the present invention because alfalfa is a hardy, perennial plant, which grows well with minimal fertilization and irrigation. Alfalfa is also a very prolific plant. In temperate areas such as those found in the Midwestern United States, alfalfa will yield three or more harvests per growing season. Methods have also been developed for wet fractionation of the herbage matter to recover value-added products therefrom.

Tobacco is equally preferred for its prolific growth, ease of transformation, and its well-characterized genetics. Both alfalfa and tobacco are widely cultivated throughout the United States and in other parts of the world.

In the most preferred embodiment, alfalfa or tobacco plants are stably transformed to express, constituitively, enzymatically active E2 or E3 cellulases from *T. fusca*. Also preferred are alfalfa or tobacco which express enzymatically active CBH I from *T. reesei* or combinations of E2, E3, and CBH I. The *T. fusca* cellulases are most preferred because they are native to thermo-tolerant bacteria and are relatively heat stable. This allows isolation of the cellulase from plant material using relatively rigorous heat precipitation without adversely effecting the activity of the cellulase.

Stage-Specific and Tissue-Specific Expression of Cellulases:

Because the enzymes to be expressed by the transformed plant hosts hydrolyze components of the plant cell wall, high levels of expression might have a deleterious effect on the plant host. Therefore, targeting of the expressed enzyme to particular sub-cellular compartments may be preferred. Targeting of the expressed enzyme may also be preferred to avoid expression of the enzyme in sub-cellular compartments where proteolytic activity is high. Targeting of the expressed enzyme may also be preferred if the exogenous cellulase activity interferes with the normal cellular metabolism of certain compartments.

For instance, targeting expression to the apoplast allows the exogenous protein to avoid the more active protein-degrading systems of other cellular compartments, such as in plant leaf vacuoles.

Several signal sequences are known and can be utilized in the present invention. For example, signal sequences for targeting to the secretory pathway are known, Wandelt et al. (1992), Bednarek (1991), Mason et al. (1988), as are sequences for targeting to the chloroplast, Keegstra et al. (1993), and the mitochondrion, de Castro Silva Filho et al. (1996).

For apoplast targeting, the VSP leader is preferred. The VSP leader comprises the amino acid sequence: $NH_3$-Met-Lys-Leu-Phe-Val-Phe-Phe-Val-Ala-Ala-Val-Val-Leu-Val-Ala-Trp-Pro-Cys-His-Gly-Ala- (SEQ. ID. NO: 3). See Mason et al. (1988).

Additionally, bacterial secretory sequences found in the wild-type cellulase gene may be removed to afford cytoplasmic expression of the enzyme in the recombinant plant host.

Targeting can be achieved by fusing combinations of mitochondrial and chloroplast targeting signals to the N-terminus of the desired cellulase, as has been demonstrated for the reporter genes chloramphenicol acetyl transferase and β-glucuronidase, de Castro Silva Filho et al. (1996). In some cases, efficient translocation requires the presence of both signal peptides, with the amino terminal peptide being crucial in specifying import into a particular organelle. In addition, vacuole targeting can be achieved by fusing the sequence encoding the N-terminal 146 amino acids of the vacuolar patatin protein between a secretory leader and structural gene for the cellulase, as has been demonstrated for the yeast invertase gene, Sonnewald et. al. (1991).

Regeneration of Mature Transgenic Plants:

Transgenic tobacco and alfalfa were produced by Agrobacterium-mediated transformation using explants as source material. This is a routine method easily followed by those skilled in the art. The production methods for transgenic tobacco and alfalfa are given as non-limiting illustrations of the practice of the invention.

The transformation procedure for tobacco is essentially the explant method developed by Horsh et al. (1985). Leaf explants are taken from the second and third fully expanded leaves of three-week old in vitro shoot cultures of *Nicotiana tabacum* W38 maintained on MS medium, Murashige and Skoog (1962). The leaf pieces are cut into 1 cm squares and pre-cultured on MS medium with 2.0 mg/L 6-benzyl-aminopurine (BAP) and 0.1 mg/L alpha-naphthalene acetic acid (NAA) for 24 hours at 25° C. with a 16 hour photo period of 70–90 $\mu$E $m^{-2}s^{-1}$. After pre-culture, explants are placed into a suspension of Agrobacterium cells. After 30 minutes, leaf explants are blotted on filter paper and placed abaxial-side down on MS medium with 1.0 mg/L BAP and 0.1 mg/L NAA and co-cultivated for four days under the same conditions as given above. Leaf pieces are then rinsed three times in sterile water, blotted on filter paper, and transferred to the media used for co-cultivation but containing 100 mg/L kanamycin and 400 mg/L carbenicillin. Plantlets (typically 2–3) develop 10–14 days later from callus formed along cut leaf edges. If desired, further plantlet formation can be achieved by transfer of explants to fresh medium at two week intervals. Plantlets are excised and rooted on MS media containing 100 mg/L kanamycin and 400 mg/L carbenicillin.

To transform alfalfa, new-growth trifoliates are taken from alfalfa plants (regenerable genotypes, Bingham et al. (1975)) maintained in a growth room and sterilized using alcohol and bleach washes (30 seconds in 70% alcohol, 90 seconds in 20% hypochlorite+0.1% SDS, followed by three rinses in sterile distilled water). Leaf edges are cut on moist filter paper and tissue then placed into liquid SH-II medium. (Bingham et al., supra.) When sufficient explants have been taken, the explants are moved to a suspension of Agrobacterium cells containing the engineered plasmid. (The Agrobacterium suspension is taken from an overnight culture grown in liquid YEP selection medium.) Cell density is adjusted to fall between about 0.6 to about 0.8 at $A_{660}$. After 30 minutes inoculation, the explants are gently blotted on filter paper and placed on B5H medium, Brown and Atanassov (1985), for four days. They are then rinsed twice in sterile water and cultured on B5H for a further four days. At the end of this period, they are rinsed three times and transferred to B5H containing 25 mg/L kanamycin and 250 mg/L carbenicillin. Plates are maintained at 24° C., 16 hour photo period, light intensity 60–80 $\mu$E $m^{-2}s^{-1}$. Explant-derived calli (and occasionally embryoids) which form within 3 weeks on this medium are moved to B5H with antibiotics but without hormones to allow for further embryoid production and development of existing embryoids. After three to four weeks, embryos are transferred to MS medium including the two antibiotics to allow for development into plantlets. Callus forms on untreated explants in the presence of 25 mg/L kanamycin but embryos are never produced. Each explant piece can give rise to multiple (up to 40) embryos. Plantlets are rooted on MS medium lacking antibiotics.

Monitoring Cellulase Expression:

Cellulase expression can be monitored using a number of different methods, the two most common being western blot analysis (which detects cellulase protein using antibodies specific for the cellulase of interest) and zymographic analysis or enzyme assay (both of which measure the ability of the expressed cellulase to degrade a cellulosic substrate).

Briefly, in the western blot technique, whole plant samples (or root tips, leaves, etc.) are ground in an extraction buffer (preferably 50 mM sodium acetate (pH 5.5) and 10 mM dithiothreitol) and an aliquot of the extract loaded onto an electrophoresis gel (e.g., polyacrylamide containing SDS). Preferably, identical extractions are performed on non-transformed plants and aliquots of these extractions are then loaded onto parallel lanes of the gel to act as negative controls. Serial dilutions of purified cellulase standards can be also electrophoresed to act as positive controls. The gel is then subjected to electrophoresis in standard and well known fashion.

After electrophoresis is complete, the separated proteins are electro-transferred to a nitrocellulose, PVDF, or nylon membrane, in well known fashion. The membrane containing the immobilized proteins is then immersed in a non-specific blocking buffer or detergent (e.g., "TWEEN 20"), and then placed in a solution containing an antibody (the primary antibody) which is specifically reactive with the particular cellulase under investigation. The membrane is then washed and exposed to an enzyme-antibody conjugate directed against the primary antibody (e.g., goat anti-rabbit IgG). The membrane is then exposed to a chromogenic or luminescent substrate to visualize cellulase hybridization on the membrane.

Zymograms in which the cellulase of interest is resolved in a gel system and then assayed for activity within the gel provide a relatively simple way to assess the activity of cellulases in crude cell lysates. See Coughlan (1988). In this approach, plant tissue is ground in the presence of an appropriate grinding buffer (100 mM Tris-HCl pH 9.0, 5 mM 2-mercaptoethanol, 1 mM phenylmethanesulfonyl fluoride, 0.5 mM ethylenediamine-tetraacetic acid, for example). After grinding of the tissue, an equal volume of a 50% (v/v) slurry of washed polyvinylpolypyrrolidone (suspended in grinding buffer) is added and mixed thoroughly. After centrifugation of the mixture, a sample of the cleared extract is subjected to electrophoresis through a non-denaturing (8%, w/v) polyacrylamide gel. The resulting gel is used to prepare a sandwich with a thin film (<2 mm) of agarose (0.7% agarose, 0.5% Sigma medium viscosity carboxymethycellulose) bonded to "GELBOND" film (FMC Corporation). After incubation for 1.5 hours at 50° C., the agarose film is stained with "CONGO RED" dye for 30 minutes followed by a 1M NaCl wash. After several minutes, it is possible to visualize cellulase activity as a clear zone within a background of red staining.

Cellulase activity is most commonly assayed in aqueous solution, using a cellulosic substrate and monitoring the reaction for either the release of a chromophore/fluorophore or release of cellobiose ("reducing sugar"). For example, *T. fusca* E2 activity can be measured by incubating a sample of the enzyme in a 0.4 ml reaction containing 1% (w/v) low viscosity carboxymethylcellulose (Sigma C-5678) and 50 mM NaOAc pH 5.5 at 55° C. for 2–20 hours. 1.0 ml of DNS solution, see Irwin et al. (1993), is then added and the mixture is boiled for 15 minutes. Measurement of absorbance values at 600 nm for each reaction can then be correlated to values determined for a known series of glucose standards to determine the extent of carboxymethylcellulose hydrolysis. For plant extracts, background values are determined by preparing parallel reaction samples which contain no substrate and subtracting this value from that obtained in the presence of 1% carboxymethylcellulose.

For a more complete discussion of cellulase assays, see Adney et al. (1994), Baker et al. (1992), Tucker et al. (1989) and Irwin et al. (1993).

Isolation of Cellulase Activity from Plants:

It is most preferred that, where applicable, the enzyme not be purified from the plant material, but rather that the plant material containing the cellulase activity be used directly. This is demonstrated in the Examples, below, where transgenic alfalfa which expressed cellulase activity is added directly to silage materials to further the extent of fermentation.

If isolation of the cellulase activity is desired, this can be accomplished by any means known to the art. For example, the preferred *T. fusca* E2, E3, and CBH I enzymes are taken from thermo-tolerant bacteria. The activity of these enzymes remains unchanged by treatments up to about 55–60° C. Therefore, these enzymes can be isolated by gently heating the plant material in aqueous buffered solution (100 mM Tris/HCl pH 9.0, for example) to precipitate the bulk of plant proteins. The soluble cellulase enzymes are then recovered and further purified by any means known to the art, including HPLC, affinity chromatography, and the like. To facilitate downstream processing of the enzyme, a purification tag may optionally be incorporated into the expressed cellulase.

Since the above-mentioned enzymes are well-characterized, the preferred purification scheme is based on established protocols already in existence. For example, *T. fusca* E2 from a heat-treated plant extract is further purified by adsorption to a phenyl "SEPHAROSE" column in the presence if 0.8 M ammonium sulfate. Successive column washes using ammonium sulfate concentrations of 0.6 M and 0.3 M in a buffer containing 5 mM KPi, pH 6.0 and 5 mM NaCl are followed by a final wash with 0.1 M KPi, pH 6.0. Elution of E2 is accomplished using 5 mM KPi, pH 6.0. Peak fractions are loaded on a hydroxylapatite column (equilibrated with 1 mM KPi, pH 6.0) and the flow-through fractions collected and pooled. The pooled fractions are loaded on a "Q-SEPHAROSE" column (pre-equilibrated with 10 mM BisTris, pH 6.0) and eluted with a continuous buffer gradient from 5 mM BisTris, pH 6.0 to 150 mM NaCl, 5 mM BisTris, pH 6.0. Peak fractions from the "Q-SEPHAROSE" column are then pooled, concentrated and stored frozen in convenient aliquots. Similarly detailed protocols exist for both *T. fusca* E3 and *T. reesei* CBH I, see Irwin et al. (1993).

EXAMPLES

The following Examples are included solely to aid in a more complete understanding of the manufacture and use of the transgenic plants disclosed and claimed herein. The Examples do not limit the scope of the invention in any fashion.

Example 1

Production of Transgenic Alfalfa and Tobacco which Express Cellulase "E2" of *T. fusca*

Transgenic alfalfa and tobacco plants were produced using the same protocol. Binary vectors carrying recombinant cellulase expression cassettes were transformed into *Agrobacterium tumefaciens* strain LBA 4404, facilitating Agrobacterium-mediated transformation of plant tissue. The construct used is shown in FIG. 1. The gene encoding the E2 cellulase of *Thermomonospora fusca* was obtained as described by Ghangas & Wilson (1988). The E2 gene was modified by PCR using the XbaE2 primer, 5'-GCTCTAGATGAATGATTCTCCGTTC-3' (SEQ. ID.

NO: 4) and the "−20 sequencing primer," 5'-TGACCGGCAGCAAAATG-3' (SEQ. ID. NO: 5), (product #1211, New England Biolabs, Inc., Beverly, Mass.), resulting in a recombinant gene in which an Xba I site (bold italics) was incorporated immediately 5' to an introduced start codon (underlined). This start codon precedes the first codon encoding the mature form of the E2 protein (AAT, nt's 348–350 in SEQ. ID. NO: 1). The net effect of these changes is the removal of the bacterial secretion signal peptide (resulting in cytosolic accumulation), the addition of a novel cloning site to facilitate expression cassette construction and the addition of a methionine residue to the N-terminus of the protein compared to the processed mature form of E2 obtained from *T. fusca*).

The cloned E2 gene required no modification at the 3' end as a convenient Eco RI restriction site occurs approximately 45 nucleotides 3' to the stop codon.

The preferred expression cassette includes the hybrid "MAC" promoter and the mannopine synthetase terminator. The MAC promoter contains distal elements, including the transcriptional enhancer, of the CaMV 35S promoter (−940 to −90, relative to the mRNA start site), as well as proximal promoter elements derived from the Agrobacterium mannopine synthetase promoter (−301 to +65 relative to the mRNA start site). MAC has been reported to result in higher levels of expression than either of the natural promoters (Comai et al. (1990).) The expression cassette was cloned into the pCGN1578 binary vector and mobilized into Agrobacterium.

Figure 3:
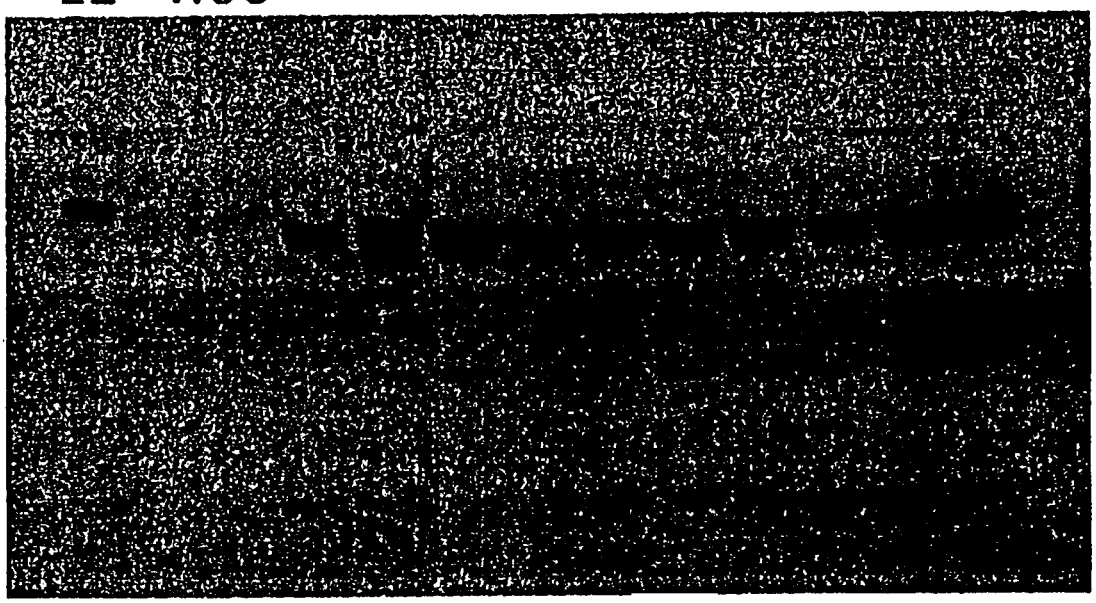
FIG. 3 is a western blot analysis evidencing the expression of *T. fusca* E2 cellulase in tobacco transformed to contain the expression construct depicted in FIG. 1.

Initial tobacco transformants were screened by western blot to determine the level of expression. Levels of expression ranged up to 0.1 to 0.2% of extracted protein. The mature plants were allowed to self and set seed. One of the initial transformants, designated CT30, was tested further to verify the sexual transmission of the transgene. S1 seeds from this plant were germinated and tested for kanamycin resistance. Leaf samples from kan$^R$ seedlings as well as a W38 control were prepared for western blot analysis as described previously. The results are depicted in FIG. 3. Each lane contained extract corresponding to 5 mg fresh weight of leaf tissue. In addition, 1 ng of purified E2 enzyme was loaded as a control. Levels of expression were similar to that observed in the parental transformant, demonstrating the stable sexual transfer of this trait. Similar genetic stability was also observed in alfalfa plants transformed with this transgene.

Figure 5:
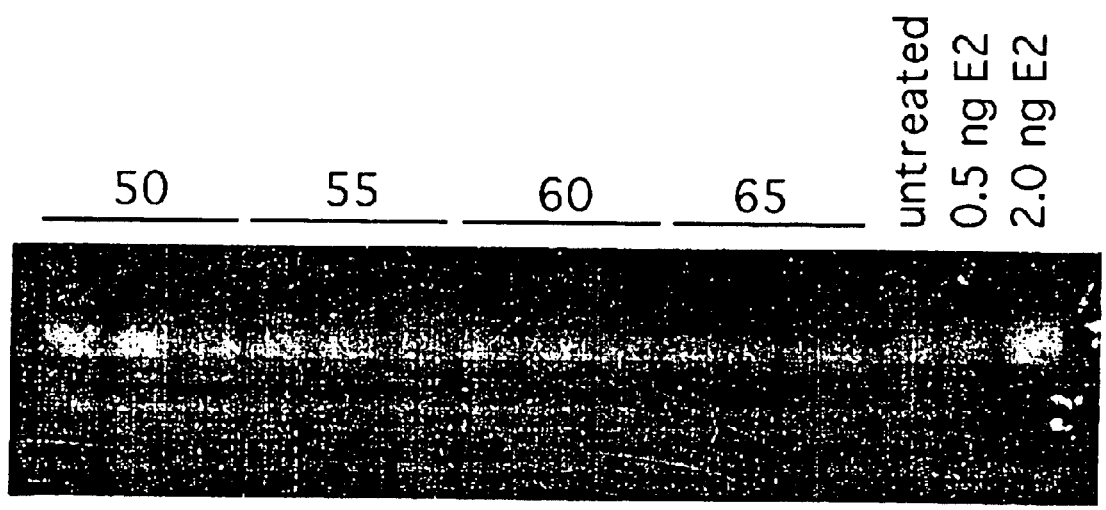
FIG. 5 is a zymogram gel assay evidencing the expression of active *T. fusca* E2 cellulase in alfalfa transformed to contain the expression construct depicted in FIG. 1.

The thermal stability and enzymatic activity of recombinant *T. fusca* E2 was demonstrated using transgenic alfalfa. Samples were prepared for zymogram analysis as described above. As shown in FIG. 5, aliquots of alfalfa extract were treated for 5, 10 and 20 minutes (grouped from left to right) at each of the temperatures indicated (° C.) before being subjected to native gel electrophoresis. An untreated sample of extract and two purified E2 standards were included as controls. Levels of E2 activity corresponded well with expected activity based on western blot analysis of samples from the same plant. In addition, no significant loss in band intensity (activity) was observed at any of the treatment temperatures, despite the fact that greater than 95% of the soluble protein in the extract is denatured after 20 minutes at 65° C.

Example 2

Production of Transgenic Alfalfa and Tobacco which Express Cellulase "E3" of *T. fusca*

Here, the expression construct depicted in FIG. 2 was used to transform alfalfa and tobacco using the same methodology as described in Example 1.

The gene encoding the E3 cellulase of *Thermomonospore fusca* was obtained as described by Zhang et al. (1995). The 5' end of the E3 gene was modified by PCR using the primer XbaE3, 5'-GCTCTAGATGCCGGCTGCTCGGTG-3' (SEQ. ID. NO: 6), resulting in a recombinant gene in which an Xba I site (bold italics) was incorporated immediately 5' to an introduced start codon (underlined). This start codon precedes the first codon encoding the mature form of the E3 protein (GCC, nt 689–691 in SEQ. ID. NO: 2). The 3' end of the E3 gene was modified using the primer RIE3, 5'-GGAATTCTTACAGAGGCGGGTAG-3' (SEQ. ID. NO: 7), thereby placing an Eco RI restriction site (bold italics) immediately 3' to the stop codon (underlined) for the E3 gene. Note that this latter primer is homologous to the noncoding strand of the E3 gene. The net effect of these changes is the removal of the bacterial secretion signal peptide (resulting in cytosolic accumulation), the addition of novel cloning sites to facilitate expression cassette construction and the addition of a methionine residue to the N-terminus of the protein (compared to the processed, mature form of E3 obtained from *T. fusca*).

The E3 expression cassette was constructed as described above for the E2 cassette.

Figure 4:
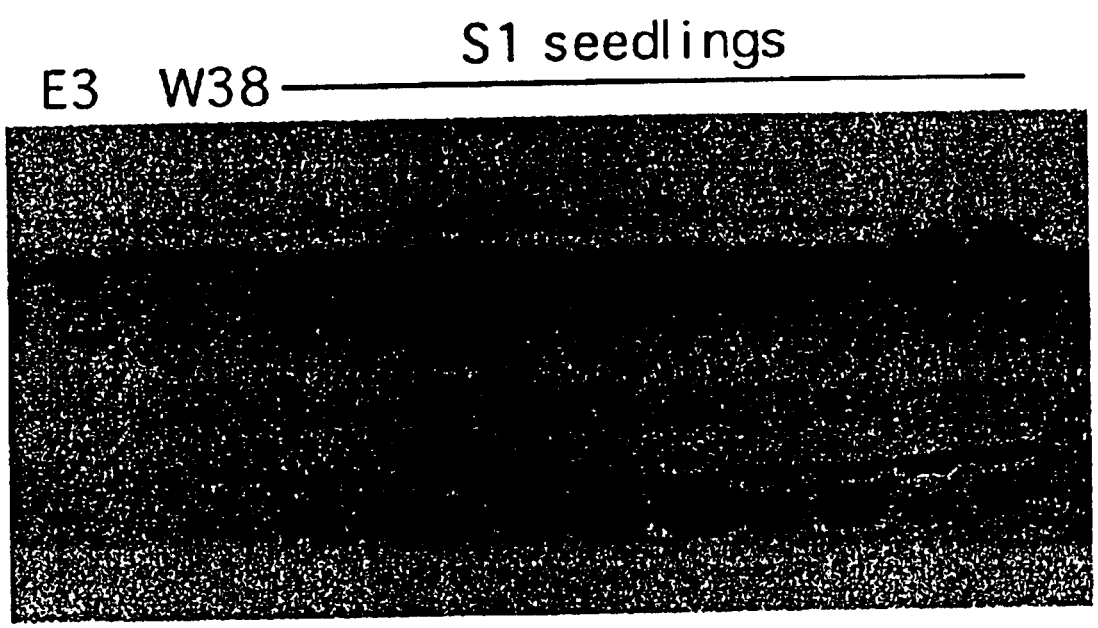
FIG. 4 is a western blot analysis evidencing the expression of *T. fusca* E3 cellulase in tobacco transformed to contain the expression construct depicted in FIG. 2.

Initial tobacco transformants were screened by western blot to determine the level of expression. Levels of expression ranged up to about 0.04% of extracted protein. The mature plants were allowed to self and set seed. One of the initial transformants, designated CT117, was tested further to verify the sexual transmission of the transgene. S1 seeds from this plant were germinated and tested for kanamycin resistance. Leaf samples from kan$^R$ seedlings as well as a W38 control were prepared for western blot analysis as described previously. The results are depicted in FIG. 4. Each lane contained extract corresponding to 5 mg fresh weight of leaf tissue. In addition, 1 ng of purified E3 enzyme was loaded as a control. Levels of expression were comparable to that observed in the parental transformant, demonstrating the stable sexual transfer of this trait.

Example 3

Sexual Transfer of Cellulase Expression in Tobacco and Alfalfa

Original transgenic lines of tobacco and alfalfa shown to express either E2 or E3 cellulase were used in sexual crosses. In both cases, the trait segregated in progeny as predicted by Mendelian genetics. Expression levels were the same as, or greater than those seen in parental lines.

Example 4

Use of Transgenic Alfalfa in Silage

Here, regular non-transformed alfalfa, alfalfa transformed according to Example 1 and alfalfa transformed according to Example 2 were ensiled under identical conditions for one month and the products of fermentation for each experiment quantified. The results are presented in Table 2.

All of the ensiled plant material was ground separately through a manual meat grinder. The grinder was rinsed with water and wiped with ethanol after grinding each sample. A 1 to 1 to 1 mixture of non-transformed alfalfa, E2-transformed alfalfa, and E3-transformed alfalfa was ground together and used to assemble two control silos (Cont1 and Cont2, 50 g each). The two control silos were inoculated with a 1 mL of a commercial inoculant (0.1098 g "BIOMATE LP/PC" concentrate in 500 mL sterile water).

Two silos each of E2-transformed alfalfa (E2-1, E2-2) and E3-transformed alfalfa (E3-1, E3-2) were constructed in the same fashion as the controls (35 g each, inoculated with 0.6 mL of the above-noted inoculant). Two silos of mixed E2- and E3-transformed alfalfa were constructed by grinding together 17.5 g each of E2- and E3-transformed alfalfa per silo (35 g each, inoculated with 0.6 mL of the above-noted inoculant).

All of the silos were then placed into a 30° C. water bath until opening.

Of special note in this Example is the increased amount of fermentation products in the transgenic alfalfa as compared to the non-transformed alfalfa. In particular, note that a mixture of alfalfa herbage expressing both the E2 and E3 cellulases exhibits markedly improved fermentation yield as compared to the non-transformed alfalfa and ensiled alfalfa expressing either E2 or E3 enzymes.

Clearly, as shown by this Example, expression of cellulases in transgenic alfalfa leads to better silage production.

pBI121 (Clontech Labs, Palo Alto, Calif.) as a XbaI to SacI fragment, replacing the uidA gene and placing the new construct (designated pZ49.1) under the control of the CAMV 35S promoter.

An analogous construct (designated pZ57.1) was generated in which the E1 coding sequence was truncated to yield the E1 catalytic domain (E1cd) using the NarE1 primer (SEQ. ID. NO: 10) and the SacE1cd primer, 5'-TGGAGCTCTAGACAGGATCGAAAAT-3' (SEQ. ID. NO: 12). This construct encodes a polypeptide containing the VSP leader peptide (SEQ. ID. NO: 13) fused to the first 358 amino acids of the E1 protein. The codon specifying valine 358 is bold, italics (note that this oligonucleotide represents the "antisense" strand). Plasmids pZ49.1 and pZ57.1 were transformed into *Agrobacterium tumefaciens* strain LBA4404 to yield strains PZA8 and PZA9, respectively.

Putative transgenic tobacco plants were screened by a combination of Western blotting and E1 activity assay. Leaf samples were removed from plants grown in Magenta boxes

TABLE 2

Organic Acid Analysis (OAA) via HPLC

| Sample ID | % DM | pH | SUC | LAC | FOR | ACE | PRO | 2,3But | ETOH | BUT | Total Prod. | Avg. Total Prod. |
|---|---|---|---|---|---|---|---|---|---|---|---|---|
| Cont 1 | 23.33612 | 5.741 | 0.144 | 2.014 | 0.000 | 1.764 | 0.000 | 0.239 | 0.704 | 0.000 | 4.86 | 5.47 |
| Cont 2 | 21.62983 | 5.121 | 0.159 | 3.885 | 0.000 | 1.407 | 0.328 | 0.000 | 0.294 | 0.000 | 6.07 | |
| E2-1 | 22.99369 | 5.277 | 0.157 | 3.390 | 0.000 | 2.300 | 0.233 | 0.000 | 0.330 | 0.000 | 6.41 | 6.09 |
| E2-2 | 23.83774 | 5.166 | 0.361 | 2.935 | 0.000 | 1.998 | 0.177 | 0.000 | 0.298 | 0.000 | 5.77 | |
| E3-1 | 22.88773 | 5.128 | 0.283 | 3.321 | 0.000 | 2.380 | 0.177 | 0.000 | 0.292 | 0.000 | 6.45 | 6.61 |
| E3-2 | 22.22822 | 5.151 | 0.354 | 3.324 | 0.000 | 2.608 | 0.200 | 0.000 | 0.288 | 0.000 | 6.77 | |
| E23-1 | 22.95945 | 5.743 | 0.551 | 2.848 | 0.000 | 3.185 | 0.328 | 0.000 | 0.337 | 0.000 | 7.25 | 7.45 |
| E23-2 | 22.66411 | 5.888 | 0.602 | 2.745 | 0.000 | 3.649 | 0.301 | 0.000 | 0.353 | 0.000 | 7.65 | |

The table headings are as follows:
% DM = percent dry matter of silage, pH = acidity, SUC = succinic acid, LAC = lactic acid, FOR = formic acid, ACE = acetic acid, PRO = propionic acid, 2,3But = 2,3-butanediol, ETOH = ethanol, BUT = butyric acid, Cont 1 and Cont 2 = controls, E2-1 and E2-2 = transformant expressing E2, E3-1 and E3-2 = transformants expressing E3, E23-1 and E23-2 = a 1:1 mixture of herbage from transgenic alfalfa expressing E2 and E3.

Example 5

Production of Transgenic Tobacco Plants which Express Cellulase "E1" of *A. cellulolyticus*

Figure 6A:
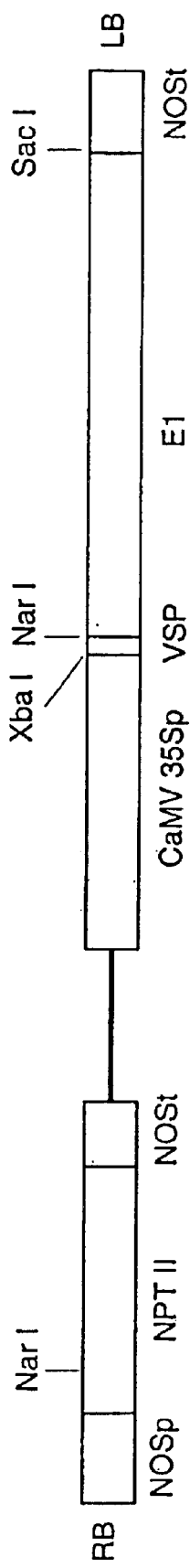
FIG. 6A is a schematic diagram of a binary vector T-DNA for an expression construct to transform plants to contain cellulase E1 of *A. cellulolyticus*.
Figure 6B:
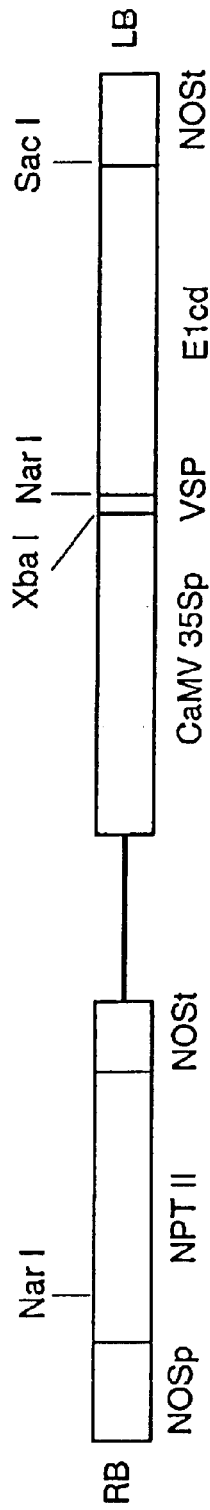
FIG. 6B is a schematic diagram of a binary vector T-DNA for an expression construct to transform plants to contain the catalytic domain (E1cd) of cellulase E1 of *A. cellulolyticus*.

Transgenic tobacco plants were produced in a manner analogous to that described in Examples 1 and 2. Binary vectors carrying recombinant cellulase expression cassettes were transformed into *Agrobacterium tumefaciens* strain LBA 4404, thereby facilitating Agrobacterium-mediated transformation of plant tissue. The constructs for this Example are depicted schematically in FIGS. 6A and 6B. The gene encoding the E1 cellulase of *Acidothermus cellulolyticus* was obtained as described previously by Himmel et al. (see U.S. Pat. No. 5,275,944). The E1 gene was then modified by PCR using the NarE1 primer, 5'-CGGGGCGCCGGCGGCGGCTAT-3'(SEQ. ID. NO: 10) and the SacE1 primer, 5'-CCGAGCTCTTAACTTGCTGC-3' (SEQ. ID. NO: 11) to generate a recombinant E1 gene. The recombinant gene has a NarI site at the 5' end and a SacI site at the 3' end (restriction sites are underlined) to facilitate fusion to the VSP leader coding sequence (SEQ. ID. NO: 3) and nopaline synthetase terminator.

As in the previous Examples, PCR-derived fragments were sequenced to verify that no errors (mutations) had been introduced. The resulting cassette includes the VSP leader sequence operationally linked to the "mature" portion of the E1 coding sequence. This cassette was then cloned into (MS medium). Samples were ground in E1 grinding buffer (50 mM NaOAc pH 5.5, 100 mM NaCl, 10% (v/v) glycerol, 1 mM ethylenediamine-tetraacetic acid, 1 mM phenylmethanesulfonyl fluoride, 1 mg/l aprotinin, 1 mg/l leupeptin, 1 mg/l pepstatin), added at a ratio of 2 μl per mg of sample. Samples of extract were centrifuged at >10,000×G for 5 minutes to remove insoluble material and diluted 100-fold in E1 grinding buffer to which acetylated bovine serum albumin had been added (0.1 mg/ml final concentration). Diluted extract was assayed for activity at 65° C. using β-D-cellobiopyranoside (MUCB) as a substrate (0.5 mM MUCB, 50 mM NaOAc pH 5.5, 100 mM NaCl).

Reactions were terminated by the addition of an equal volume of 150 mM glycine/NaOH (pH 10). Fluorescence at 460 nm was quantified using a commercial plate reader ("BIOLUMIN 960," Molecular Dynamics) with excitation set at 355 nm. Enzyme activity in extracts was then compared to the activity of purified E1 holoenzyme and E1 catalytic domain (generously provided by Steve Thomas, National Renewable Energy Laboratory, Golden, Colo.).

In addition, a set of 4-methylumbelliferone standards was also assembled for use as calibration standards. The same extracts were also subjected to analysis by Western blotting. Both PZA8- and PZA9-transformed tobacco plants accumulated an immunoreactive species that co-migrates with purified E1cd. Very little full-length E1 is present in PZA8 transformants, indicating that proteolytic processing of the E1 enzyme is taking place. For this reason, activities are reported as E1cd equivalent, even in those plants that contain an intact E1 coding sequence. For PZA8 transformants, the average E1 expression level was 0.10% of total soluble protein, with the highest expressing plant accumulating E1 at 0.33% of total soluble protein (see FIG. 8A). E1 expression was higher in PZA9 transformants, with an average expression level of 0.21% of total soluble protein and a high value of 0.59% (See FIG. 8B).

Example 6

Production of Transgenic Tobacco Plants which Express Cellobiohydrolase I (CBH I) of *Trichoderma reesei*

Figure 7:
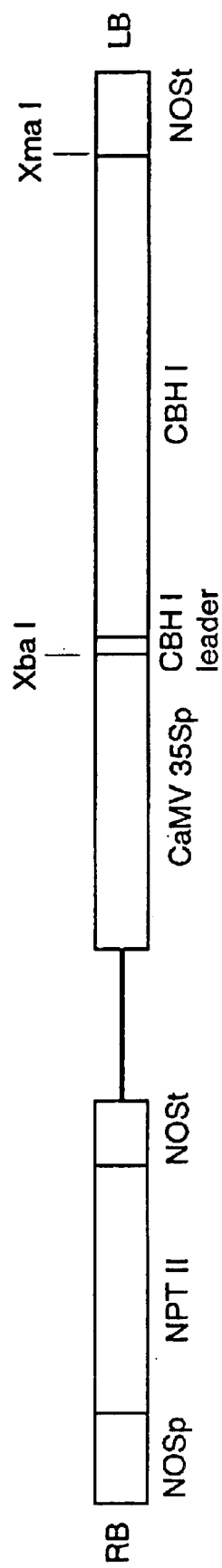
FIG. 7 is a schematic diagram of binary vector T-DNA for an expression construct to transform plants to contain cellulase CBH I of *T. Reesei*.

Transgenic plants were generated essentially as described in Example 5. A schematic diagram of the construct used is shown in FIG. 7. The gene encoding CBH I of *Trichoderma reesei* (SEQ. ID. NO: 9) was generously provided by Steve Thomas (National Renewable Energy Laboratory, Golden, Colo.) and is substantially the same as the gene described by Shoemaker et al. with its introns removed. Sequence data obtained by the inventors and by NREL scientists indicates that the gene used in this Example differs from the Shoemaker et al. sequence at nucleotide 1429. Specifically, the gene used here contains a 4 base-pair sequence (CGCC) inserted in place of G1429, thereby effectively inserting an additional codon and replacing Arg459 with two prolines. A similar substitution exists in a related CBH I enzyme from *Trichoderma viride* (see Cheng et al., 1990). The gene used here also has a silent mutation in the codon specifying Thr41 (ACT changed to ACG).

The CBH I gene was modified by PCR using the cbh2-2 primer, 5'-GCTCTAGATGTATCGGAAGTTGGC-3'(SEQ. ID. NO: 14) and the cbh3-1 primer, 5'-CCCCCGGGTTACA GGCACTGAGAG-3' (SEQ. ID. NO: 15) to generate a recombinant CBH I gene which retains its secretory leader peptide. The recombinant gene has an XbaI site at the 5' end and a XmaI site at the 3' end (restriction sites are shown in underline, start codon is bold, italics) to facilitate vector construction. The gene was cloned into pBI121 (Clontech) as a XbaI to XmaI fragment, replacing the uidA gene and placing the CBH I gene under the control of the CaMV 35S promoter.

Putative transgenic tobacco plants were screened by Western blotting. Leaf samples were removed from plants grown in Magenta boxes (MS medium) and ground in E1 grinding buffer (see composition in Example 5), added at a ratio of 2 µl per mg of sample. The extract was centrifuged at >10,000×G for 5 minutes to remove insoluble material and a portion prepared for SDS-PAGE and subsequent blotting and detection. See FIG. 9, which depicts the SDS-PAGE gel. Of 12 plants screened in this way, 3 had detectable expression (about 0.01% of total soluble protein). In addition, immunoreactive material migrated slightly ahead of the RuBisCo large subunit, consistent with the expected mobility of the 48 kDa catalytic domain (Divne et al., 1994). This suggests that CBH I, like *A. cellulolyticus* E1, is proteolytically cleaved by a plant protease.

Example 7

Production of Transgenic Tobacco Plants which Express the Endoglucanase Encoded by the cenA Gene of *Cellulomonas fimi*

In a manner analogous to the previous Examples, the cenA gene of *Cellulomonas fimi* (Wong et al., 1986) can be expressed in tobacco. A schematic diagram of the construct used is shown in FIG. 10. The cenA gene (SEQ. ID. NO: 16) is modified by PCR using the cenApst primer, 5'-GGCTGCAGGCGGCTGCCGCGTCGAC-3' (SEQ. ID. NO: 17) and the cenAsac primer, 5'-CCGAGCTCTCACCA CCTGGCGTT-3' (SEQ. ID. NO: 18) to generate a recombinant cenA gene. The recombinant gene has a PstI site at the 5' end and a SacI site at the 3' end (restriction sites are underlined, novel glycine codon in bold italics) to facilitate fusion to a VSP leader coding sequence (SEQ. ID. NO: 19) and nopaline synthetase terminator. In addition, the proline at position 2 in the mature endoglucanase enzyme is changed to a glycine, a conservative substitution. The resulting cassette consists of the VSP leader sequence fused to the "mature" portion of the cenA gene.

This cassette is then cloned into pBI121 (Clontech) as a XbaI to SacI fragment, replacing the uidA gene and placing the new construct under the control of the CaMV 35S promoter. As in the previous Examples, *Agrobacterium tumefaciens* strain LBA4404 is transformed with the resulting binary vector and subsequently used to transform plants.

Example 8

Production of Transgenic Tobacco Plants which Express Endoglucanase D, Encoded by the celD Gene of *Clostridium thermocellum*

In a manner analogous to the previous Examples, the celD gene of *Clostridium thermocellum* (see Joliff et al., 1986) can be expressed in tobacco. A schematic diagram of the construct used is shown in FIG. 11. The celD gene (SEQ. ID. NO: 20) is modified by PCR using the celDpst primer, 5'-AGCTGCAGAAATAACGG-3' (SEQ. ID. NO: 21) and the celDsac primer, 5'-CCGAGCTCTTATATTGGTAA TTTCTC-3' (SEQ. ID. NO: 22) to generate a recombinant celD gene. The recombinant gene has a PstI site at the 5' end and a SacI site at the 3' end (restriction sites are underlined) to facilitate fusion to the VSP leader coding sequence (SEQ. ID. NO: 19) and nopaline synthetase terminator. The resulting cassette includes the VSP leader sequence fused to the "mature" portion of the celD gene. Subsequent manipulations are be carried out as described in the previous Examples.

Example 9

Production of Transgenic Tobacco Plants which Express Exoglucanase S, Encoded by the exgS Gene of *Clostridium cellulovorans*

In a manner analogous to the previous Examples, the exgS gene of *Clostridium cellulovorans* (see Liu and Doi, 1998) can be expressed in tobacco. A schematic diagram of the construct used is shown in FIG. 12. The exgS gene (SEQ. ID. NO: 23) is modified by PCR using the exgSnar primer, 5'-CGGGGCGCCGCACCAGTAGTGCCA-3' (SEQ. ID. NO: 24) and the exgSsac primer, 5'-CCGAGCTCTTATT TAATCTTAAGC-3' (SEQ. ID. NO: 25) to generate a recombinant exgS gene. The recombinant gene has a NarI site at the 5' end and a SacI site at the 3' end (restriction sites are underlined) to facilitate fusion to the VSP leader coding sequence (SEQ. ID. NO: 13) and nopaline synthetase terminator. The resulting cassette consists of the VSP leader sequence fused to the "mature" portion of the exgS gene. Subsequent manipulations are carried out as described previously.

Example 10

Production of Transgenic Tobacco Plants which Express Exocellulase E6, Encoded by the celF Gene of *Thermobifida fusca* (formerly *Thermomonospora fusca*)

In a manner analogous to the previous Examples, the celF gene of *Thermobifida fusca* (see Irwin et al., 1999) can be expressed in tobacco. A schematic diagram of the construct used is shown in FIG. 13. The celF gene (SEQ. ID. NO: 26) is modified by PCR using the celFpst primer, 5'-ACGCTGCAGTCGCCTGCTCGG-3' (SEQ. ID. NO: 27) and the celFxma primer, 5'-CCCCCGGGTCAGGGAG CTCCGGC-3' (SEQ. ID. NO: 28) to generate a recombinant celF gene. The recombinant gene has a PstI site at the 5' end and a XmaI site at the 3' end (restriction sites are underlined) to facilitate fusion to the VSP leader coding sequence (SEQ. ID. NO: 19) and nopaline synthetase terminator.

The celF gene itself contains two internal XmaI recognition sites, which are removed by site-directed mutagenesis. Briefly, a portion of the gene containing the sites is subcloned to pBluescript KS+ (Stratagene, La Jolla, Calif.) as a Bgl II to Xho I fragment. PCR reactions are carried out using primer 2777 (5'-GGCCACCTGGGCAGG-3', SEQ. ID. NO: 29) and the M13-20 sequencing primer (5'-GTAAAACGACGGCCAGT-3', SEQ. ID. NO: 30), thereby destroying the site at 2775 in the Genbank sequence (underline indicates mutated nucleotide).

Similarly, primer 3227 (5'-GCGACGCTCGGGCCG-3', SEQ. ID. NO: 31) and the reverse sequencing primer (5'-AACAGCTATGACCATG-3', SEQ. ID. NO: 32) destroy the site at 3227. The two overlapping amplified fragments are then purified, heated briefly to 95° C. and cooled gradually to allow annealing to occur. The annealed template is subjected to another round of PCR using the M13-20 sequencing primer (SEQ. ID. NO: 30) and the reverse sequencing primer (SEQ. ID. NO: 32). This fragment is then subcloned as a Bgl II to Xho I fragment and sequenced before being used to replace the wild-type celF sequence. Both base changes are at the 3rd position in the codon and do not alter protein sequence. The resulting cassette consists of the VSP leader sequence operationally linked to the "mature" portion of the celF gene. Subsequent manipulations are carried out as described hereinabove.

The invention is not limited to the preferred embodiments, transformation protocols, transformed plant hosts, and expression constructs explicitly described above, but encompasses all such forms thereof as are encompassed within the scope of the attached claims.

BIBLIOGRAPHY

Adney et al. (1994), Cellulase assays. In: *Enzymatic conversion of biomass for fuels production*, Eds. M. E. Himmel, J. O. Baker & R. P. Overend. ACS symposium series 566.

Aspegren et al. (1995), Secretion of a heat-stable fungal β-glucanase from transgenic, suspension-cultured barley cells. *Molecular Breeding* 1:91–99.

Baker et al. (1992), Thermal denaturation of *T. reesei* cellulases studied by differential scanning calorimetry and tryptophan fluorescence. *Apply. Biochem. Biophys.* 34:217–231.

Bednarek (1991), The barley lectin carboxy-terminal peptide is a vacuolar protein sorting determinant in plants. *The Plant Cell* 3:1195–1206.

Belkacemi et al. (1996), Enzymatic hydrolysis of timothy grass pretreated by ammonia fiber explosion. In: *Liquid fuels and industrial products from renewable resources*, Proceedings of the third liquid fuel conference, Eds. J. S. Cundiff, E. E. Gavett, C. Hansen, C. Peterson, M. A. Sanderson, H. Shapouri & D. L. VanDyne. ASAE publication 08-96 pp 232–240.

Bingham et al. (1975), Breeding alfalfa which regenerates from callus tissue in culture. *Crop Sci.* 15:719–721.

Brown and Atanassov (1985), Role of genetic background in somatic embryogenesis in *Medicago*. *Plant Cell Tissue Organ Culture* 4:107–114.

Carrer et al. (1993), Kanamycin resistance as a selectable marker for plastid transformation in tobacco. *Mol. Gen. Genet.* 241:49–56.

Castillo et al. (1994), Rapid production of fertile transgenic plants of Rye. *Bio/Technology* 12:1366–1371.

Cheng et al. (1990), *Nucl. Acids Res.* 18:5559.

Comai et al. (1990), Novel and useful properties of a chimeric plant promoter combining CaMV 35S and MAS elements. *Plant Mol. Biol.* 15:373–381.

Coughlan, M. P. (1988), Staining Techniques for the Detection of the Individual Components of Cellulolytic Enzyme Systems. *Methods in Enzymology* 160:135–144.

*Current Protocols in Molecular Biology*, Volumes 1–3, Series Editor, Virginia Benson Chanda, ©1987–1997, John Wiley & Sons, Inc.

de Castro Silva Filho et al. (1996), Mitochondrial and chloroplast targeting sequences in tandem modify protein import specificity in plant organelles. *Plant Mol. Biol.* 30:769–780.

Divne et al. (1994), The three-dimensional crystal structure of the catalytic core of cellobiohydrolase I from *Trichoderma reesei*. *Science* 265:524–528.

Ghangas & Wilson (1988), Cloning of the *Thermomonospora fusca* endoglucanase E2 gene in *Streptomyces lividans*: Affinity purification and functional domains of the cloned gene product. *Appl. Envir. Microbiol.* 54:2521–2526.

Grohmann et al. (1992), Potential for fuels from biomass and wastes. In: *Emerging technologies for materials and chemicals from biomass*, Eds. R. M. Powell, T. P. Schultz and R. Narayan. ACS symposium series 576.

Henrissat et al. (1995), Synergism of cellulases from *Trichoderma reesei* in the degradation of cellulose. *Bio/Technology* 3:722–726.

Horsh et al. (1985), A simple and general method for transferring genes into plants. *Science* 227:1229–1231.

Irwin et al. (1993), Activity studies of eight purified cellulases: Specificity, synergism, and binding domain effects. *Biotechnol. Bioeng.* 42:1002–1013.

Irwin et al. (1999), Characterization of a *Thermomonospora fusca family* 48 exocellulase E6. Direct Genbank submission AF144563.

Ishida et al. (1996), High efficiency transformation of maize mediated by *Agrobacterium tumefaciens*. *Nature Biotechnology* 14:745–750.

Joliff et al. (1986), Nucleotide sequence of the cellulase gene celD encoding endoglucanse D of *Clostridium thermocellum*. *Nucleic Acids Res.* 14:8605–8613.

Keegstra et al. (1993), Targeting of proteins into chloroplasts. *Physiologia Plantarum* 93:157–162.

Lao et al. (1991), *J. Bacteriol.* 173:3397–3407.

Liu and Doi (1998), Properties of exgS, a gene for a major subunit of the *Clostridium cellolovorans* cellulosome. *Gene* 211:39–47.

Mason et al. (1988), Proteins homologous to leaf glycoproteins are abundant in stems of dark-grown soy bean seedlings. Analysis of proteins and cDNAs. *Plant Mol. Biol.* 11:845–856.

McBride and Summerfelt (1990), Improved binary vectors for Agrobacterium mediated plant transformation. *Plant Mol. Biol.* 14:269–276.

McBride et al. (1994), Controlled expression of plastid transgenes in plants based on a nuclear DNA-encoded and plastid-targeted T7 RNA polymerase. *Proc. Natl. Acad. Sci. USA* 91:7301–7305.

Micelli et al. (1996), Integrated treatments of steam explosion and enzymatic hydrolysis to produce energetic and industrial products from lignocellulosic biomasses. *Agro-food-Industry Hi-tech* 7:25–28.

Murashige and Skoog (1962), A revised medium for rapid growth and bioassays with tobacco tissue cultures. *Physiol. Plant* 15:473–497.

Pentilla et al. (1987), *Yeast* 3:175–185.

Shoemaker et al. (1983), *Bio/Technology* 1:691–696.

Sonnewald et. al. (1991), Transgenic tobacco plants expressing yeast-derived invertase in either the cytosol, vacuole or apoplast: a powerful tool for studying sucrose metabolism and sink/source interactions. *The Plant J*. 1:95–106.

Spezio et al. (1993), Crystal structure of the catalytic domain of a thermophilic endocellulase. *Biochemistry* 32:9906–9916.

Tucker et al. (1989), Ultra-thermostable cellulases from *Acidothermus cellulolyticus* comparison of temperature optima with previously reported cellulases. *Biotechnology* 7:817–820.

Vasil et al. (1993), Rapid production of transgenic wheat plants by direct particle bombardment of cultured immature embyros. *Bio/Technology* 11:1553–1558.

Wandelt et al. (1992), Vicilin with carboxy-terminal KDEL is retained in the endoplasmic reticulum and accumulates to high levels in the leaves of transgenic plants. *Plant J*. 2:181–192.

Wong et al. (1986), Characterization of an endoglucanase gene cenA of *Cellulomonas fimi*. *Gene* 44:315–324.

Zambryski, P., J. Tempe, and J. Schell (1989), Transfer and function of T-DNA genes from Agrobacterium Ti and Ri plasmids in plants. *Cell* 56:193–201.

Zhang et al. (1995), Characterization of a *Thermomonospora fusca* exocellulase. *Biochemistry* 34:3386–3395.

What is claimed is:

1. A genetically recombinant tobacco or alfalfa plant which is stably transformed to contain and express a gene sequence which encodes *T. fusca* cellulase E2.

2. A genetically recombinant tobacco or alfalfa plant which is stably transformed to contain and express a gene sequence which encodes *T. fusca* cellulase E3.

3. The genetically recombinant plant of claim 1, which is alfalfa.

4. The genetically recombinant plant of claim 1, which is tobacco.

5. A method for producing cellulose-degrading enzymes comprising cultivating a genetically recombinant plant according to claim 1.

6. The method of claim 5, further comprising concentrating the cellulose-degrading enzymes.

7. A method of ensilement comprising ensiling a plant according to claim 1, whereby cellulose-degrading enzymes produced by the plant increase nutritional value of silage.

8. The genetically recombinant plant of claim 2, which is alfalfa.

9. The genetically recombinant plant of claim 2, which is tobacco.

10. A method for producing cellulose-degrading enzymes comprising cultivating a genetically recombinant plant according to claim 2.

11. The method of claim 10, further comprising concentrating the cellulose-degrading enzymes.

12. A method of ensilement comprising ensiling a plant according to claim 2, whereby cellulose-degrading enzymes produced by the plant increase nutritional value of silage.

* * * * *

SEQUENCE LISTING

```
<160> NUMBER OF SEQ ID NOS: 32

<210> SEQ ID NO 1
<211> LENGTH: 1621
<212> TYPE: DNA
<213> ORGANISM: Thermomonospora fusca

<400> SEQUENCE: 1
cgatatggat gatctgacgt ctgaatcccc ttgtcaccct agacattcac ccattttgtc      60
gcttttacgg ctttctttgg gagttctccg tttcaccaag gaacaaaacc gcaacggaga     120
gtaggcgcgg tctttacagc tcccttgcca atggttatcg tccgaacgga aaacgatctg     180
ggagcgctcc cagccatgcg ctcctcttcg tgcccctcac ttcttttgag ccttgtgctc     240
gttaggagcc ccgaatgtcc cccagacctc ttcgcgctct tctgggcgcc gcggcggcgg     300
ccttggtcag cgcggctgct ctggccttcc ggtcgcaagc ggcggccaat gattctccgt     360
tctacgtcaa ccccaacatg tcctccgccg aatgggtgcg gaacaacccc aacgacccgc     420 gtacccggt aatccgcgac cggatcgcca gcgtgccgca gggcacctgg ttcgcccacc      480 acaacccgg gcagatcacc ggccagatcg acgcgctcat gagcgccgcc caggccgccg      540
gcaagatccc gatcctggtc gtgtacaacg ccccgggccg cgactgcggc aaccacagca     600
gcggcggcgc ccccagtcac agcgcctacc ggtcctggat cgacgaattc gctgccggac     660
tgaagaaccg tcccgcccac atcatcgtcg ggccggacct gatctcgctg atgtcgagct     720
gcatccagca cgtccagcag gaagtcctgg agacgatggc gtacgcgggc aaggccctca     780
aggccgggtc ctcgcaggcg cggatctact tcgacgccgg ccactccgcg tggcactcgc     840
ccgcacagat ggcttcctgg ctccagcagg ccgacatctc caacagcgcg cacggtatcg     900
ccaccaacac ctccaactac cggtggaccg ctgacgaggt cgcctacgcc aaggcggtgc     960
tctcggccat cggcaacccg tccctgcgcg cggtcatcga caccagccgc aacggcaacg    1020
gccccgccgg taacgagtgg tgcgacccca gcggacgcgc catcggcacg cccagcacca    1080
ccaacaccgg cgacccgatg atcgacgcct tcctgtggat caagctgccg ggtgaggccg    1140
acggctgcat cgccggcgcc ggccagttcg tcccgcaggc ggcctacgag atggcgatcg    1200
ccgcgggcgg caccaacccc aacccgaacc ccaacccgac gccaccccc actccgaccc    1260 ccacgccgcc tcccggctcc tcggggggcgt gcacggcgac gtacacgatc gccaacgagt    1320
```

-continued

```
ggaacgacgg cttccaggcg accgtgacgg tcaccgcgaa ccagaacatc accggctgga      1380
ccgtgacatg gaccttcacc gacggccaga ccatcaccaa cgcctggaac gccgacgtgt      1440
ccaccagcgg ctcctcggtg accgcgcgga acgtcggcca acgaacg ctctcccagg        1500 gagcccccac agagttcggc ttcgtcggct ctaagggcaa ctccaactct gttccgaccc      1560
ttacctgcgc cgccagctga cccctcctgg cagtgcactg ggtggcttag cgtgctggg      1620 g                                                                     1621
```

<210> SEQ ID NO 2
<211> LENGTH: 3503
<212> TYPE: DNA
<213> ORGANISM: Thermomonospora fusca

<400> SEQUENCE: 2

```
cggcgatccc cctcatcatt caggtgcggt tagttccccc aggctaccga ggaccgaatt        60
tcggtccgtt tttcttgcgg cgagccctga daccgtttcc tgttccgttc cgtcaccatc       120
cttgcgcgtc ccggcggagg ggggaagcac cccgcgagat ggctccgcca cggcctgttt       180 ccgaccccg tcacaaaagc ccatttaacg cggtatttac aaccggtcat gaagtggcta       240
ctctcttttg ggagcgctcc cgtgccgcta gtcacactgg gacgtgaatg cgtcacggt        300 agggctcgtc gtgtgacacg cattttcgac cctgctttaa gtccctaagt gggagcgctc      360
ccagccttcg ggagaactcc cacacaacca accgtccgac gccactctcc cagcgctcaa      420
acggaggcag cagtgttcac catccccgc tcccctccgg ggcgcccggc cgtcgtccgc       480
gcaaccaccc cgaccggtcg gctgaacact gcagcgtccg gttctcgacc atccccttgc      540
gagagaacat cctccaacca aggaagaacac cgatatgagt aaagttcgtg ccacgaacag      600
acgttcgtgg atgcggcgcg ggctggcagc cgcctctgga ctggcgcttg cgcctccat       660 ggtggcgttc gctgctccgg ccaacgccgc cggctgctcg gtgtactaca cggtcaactc      720
ctggggtacc gggttcaccg ccaacgtcac catcaccaac ctcggcagtg cgatcaacgg      780
ctggaccctg gagtgggact ccccggcaa ccagcaggtg accaacctgt ggaacgggac       840
ctacacccag tccgggcagc acgtgtcgt cagcaacgcc ccgtacaacg cctccatccc       900
ggccaacgga acgttgagt tcgggttcaa cggctcctac tcgggcagca acgacatccc       960
ctcctccttc aagctgaacg gggttacctg cgacggctcg gacgaccccg accccgagcc      1020
cagcccctcc cccagcccctt cccccagccc cacagaccg gatgagccgg gcgggccgac      1080
caacccgccc accaacccccg gcgagaaggt cgacaacccg ttcgagggcg ccaagctgta      1140
cgtgaacccg gtctggtcgg ccaaggccgc cgctgagccg gcggttccg cggtcgccaa      1200 cgagtccacc gctgtctggc tggaccgtat cggcgggatc gagggcaacg acagcccgac     1260
caccggctcc atgggtctgc cgaccacct ggaggaggcc gtccgccagt ccggtggcga      1320
cccgctgacc atccaggtcg tcatctacca cctgccggc cgcgactgcg ccgcgctggc      1380
ctccaacggt gagctgggtc ccgatgaact cgaccgctac aagagcgagt acatcgaccc     1440
gatcgccgac atcatgtggg acttcgcaga ctacgagaac ctgcggatcg tcgccatcat     1500
cgagatcgac tccctgccca acctcgtcac caacgtgggc gggaacggcg gcaccgagct     1560
ctgcgcctac atgaagcaga acggcggcta cgtcaacggt gtcggctacg ccctccgcaa     1620
gctgggcgag atcccgaacg tctacaacta catcgacgcc gccaccacg gctggatcgg     1680 ctgggactcc aacttcggcc cctcggtgga catcttctac gaggccgcca acgcctccgg     1740
```

-continued

```
ctccaccgtg gactacgtgc acggcttcat ctccaacacg gccaactact cggccactgt      1800
ggagccgtac ctggacgtca acggcaccgt taacggccag ctcatccgcc agtccaagtg      1860
ggttgactgg aaccagtacg tcgacgagct ctccttcgtc caggacctgc gtcaggccct      1920
gatcgccaag ggcttccggt ccgacatcgg tatgctcatc gacacctccc gcaacggctg      1980
gggtggcccg aaccgtccga ccggaccgag ctccctccacc gacctcaaca cctacgttga      2040
cgagagccgt atcgaccgcc gtatccaccc cggtaactgg tgcaaccagg ccggtgcggg      2100
cctcggcgag cggcccacgg tcaacccggc tcccggtgtt gacgcctacg tctgggtgaa      2160
gcccccgggt gagtccgacg cgccagcga ggagatcccg aacgacgagg caagggctt       2220 cgaccgcatg tgcgacccga cctaccaggg caacgcccgc aacggcaaca accccctcgga     2280 tgcgctgccc aacgccccca ctccggcca ctggttctct gcccagttcc gcgagctgct      2340
ggccaacgcc tacccgcctc tgtaaagcgg agtgaggcaa cggctgacag cctcaacgag     2400
gaactgatca gcacctccta gccggagacg gcgcccgtcc actccccgtg ggcgggcgcc     2460
gcttttatgc cgaccgtgc cccagccgca aggggcacgg tcggcctat tccggcgatg       2520 tcggtcacgt cgccctagca cccggaaacg ccgagaaaga ctgccccgaa acggtcctct     2580
cccatccctg cattaggttg gccgagtccg cctatggctt cgtgggccgg aacccaaccc    2640
accatcaacg agaggtatca ccatggccag tgtggtgaaa ttcaatgtgc tgacggttcc    2700
tcccggtgcc ggcgccaccc cggaggacgt ttgccaagcg cgcaggcctc gtggagaacc    2760
gggccgggtt tcacgagttc caactgccgg cgcccggcga cgggacggac aagtacatcg    2820
tctacacgcg ctggcgctcc ggagaggact accagaactg gctgaacagc gaggccttcc    2880
agcgcggaca cgcccaggcc tctgaagact cccgccgcag cagccagggc ggcccggccg    2940
cgtccgcgag tgaactctgg tccttcgaag tcgtccagca cgtccaggcc caggactgat    3000
cccggtgcgg ccctcggttc tttaccgggg gccgcccacc cccttcatcc ctttttcttct    3060 cccccgcacc ccttttgatc tgcaatgatg gaattcgcga ttcttgagaa ggccgatcgt    3120
gtccatgacc gcgcagaagg caggacgacc acgcgtaccg gtcgacatcg aaggagtcaa    3180
ctgacagtgg ggactatcgc ggggctgatt gtcgcgctgt caggcgtggg gatggtctcg    3240
gccaacgtgc tcccgtggga accgtcggac ccggcatccg tggtccccgc cacctcgcag    3300
ggcagcagtt ctcccatgac gccggagccc tcgcgtcccc ggtaccccca ctcgtgcgct    3360
ccgtggtcga agaggtgccc agcgcaagcg gagaactgcg ggtcgtcgaa ggtgacgggg    3420
aggtcgtcgg cgaaggcacg ctcctgcgct acctggtgga ggtcgaagaa gggcttcccg    3480
gagaccccgc cgacttcgct gca                                              3503
```

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: VSP Leader
      Sequence

<400> SEQUENCE: 3

Met Lys Leu Phe Val Phe Phe Val Ala Ala Val Val Leu Val Ala Trp
  1               5                  10                  15

Pro Cys His Gly Ala
            20

<210> SEQ ID NO 4

-continued

```
<211> LENGTH: 25
<212> TYPE: DNA
<213> ORGANISM: Artificial Sequence
<220> FEATURE:
<223> OTHER INFORMATION: Description of Artificial Sequence: Xba E2 PCR
      Primer

<400> SEQUENCE: 4
gctctagatg aatgattctc cgttc                                              25

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Xba E2 PCR
      Primer

<400> SEQUENCE: 5
tgaccggcag caaaatg                                                       17

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Xba E3 PCR
      Primer

<400> SEQUENCE: 6
gctctagatg gccggctgct cggtg                                              25

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:  RIE3 PCR
      Primer

<400> SEQUENCE: 7
ggaattctta cagaggcggg tag                                                23

<210> SEQ ID NO 8
<211> LENGTH: 3004
<212> TYPE: DNA
<213> ORGANISM: Acidothermus cellulolyticus
<300> PUBLICATION INFORMATION:

<400> SEQUENCE: 8
ggatccacgt tgtacaaggt cacctgtccg tcgttctggt agagcggcgg gatggtcacc         60
cgcacgatct ctcctttgtt gatgtcgacg gtcacgtggt tacggtttgc ctcggccgcg        120
attttcgcgc tcgggcttgc tccggctgtc gggttcggtt tggcgtggtg tgcggagcac        180
gccgaggcga tcccaatgag ggcaagggca agagcggagc cgatggcacg tcgggtggcc        240
gatggggtac gccgatgggg cgtggcgtcc ccgccgcgga cagaaccgga tgcggaatag        300
gtcacggtgc gacatgttgc cgtaccgcgg acccggatga caagggtggg tgcgcgggtc        360
gcctgtgagc tgccggctgg cgtctggatc atgggaacga tcccaccatt ccccgcaatc        420
gacgcgatcg ggagcagggc ggcgcgagcc ggaccgtgtg gtcgagccgg acgattcgcc        480
catacggtgc tgcaatgccc agcgccatgt tgtcaatccg ccaaatgcag caatgcacac        540
atggacaggg attgtgactc tgagtaatga ttggattgcc ttcttgccgc ctacgcgtta        600
```

```
cgcagagtag gcgactgtat gcggtaggtt ggcgctccag ccgtgggctg gacatgcctg      660
ctgcgaactc ttgacacgtc tggttgaacg cgcaatactc ccaacaccga tgggatcgtt      720
cccataagtt tccgtctcac aacagaatcg gtgcgccctc atgatcaacg tgaaaggagt      780 acggggaga acagacgggg gagaaaccaa cgggggattg gcggtgccgc gcgcattgcg       840
gcgagtgcct ggctcgcggg tgatgctgcg gtcggcgtc gtcgtcgcgg tgctggcatt       900
ggttgccgca ctcgccaacc tagccgtgcc gcggccggct cgcgccgcgg gcggcggcta      960
ttggcacacg agcggccggg agatcctgga cgcgaacaac gtgccggtac ggatcgccgg     1020
catcaactgg tttgggttcg aaacctgcaa ttacgtcgtg cacggtctct ggtcacgcga     1080
ctaccgcagc atgctcgacc agataaagtc gctcggctac aacacaatcc ggctgccgta     1140
ctctgacgac attctcaagc cgggcaccat gccgaacagc atcaattttt accagatgaa     1200
tcaggacctg cagggtctga cgtccttgca ggtcatggac aaaatcgtcg cgtacgccgg     1260
tcagatcggc ctgcgcatca ttcttgaccc caccgaccg gattgcagcg ggcagtcggc      1320
gctgtggtac acgagcagcg tctcggaggc tacgtggatt ccgacctgc aagcgctggc      1380 gcagcgctac aagggaaacc cgacggtcgt cggctttgac ttgcacaacg agccgcatga     1440
cccggcctgc tggggctgcg gcgatccgag catcgactgg cgattggccg ccgagcgggc     1500
cggaaacgcc gtgctctcgg tgaatccgaa cctgctcatt ttcgtcgaag gtgtgcagag     1560
ctacaacgga gactcctact ggtggggcgg caacctgcaa ggagccggcc agtacccggt     1620
cgtgctgaac gtgccgaacc gcctggtgta ctcggcgcac gactacgcga cgagcgtcta     1680
cccgcagacg tggttcagcg atccgaccttcccaacaac atgcccggca tctgaacaa       1740 gaactgggga tacctcttca atcagaacat tgcaccggta tggctgggcg aattcggtac     1800
gacactgcaa tccacgaccg accagacgtg gctgaagacg ctcgtccagt acctacggcc     1860
gaccgcgcaa tacggtgcgg acagcttcca gtgaccttc tggtcctgga acccgattc      1920 cggcgacaca ggaggaattc tcaaggatga ctggcagacg gtcgacacag taaaagacgg     1980
ctatctcgcg ccgatcaagt cgtcgatttt cgatcctgtc ggcgcgtctg catcgcctag     2040
cagtcaaccg tccccgtcgg tgtcgccgtc tccgtcgccg agcccgtcgg cgagtcggac     2100
gccgacgcct actccgacgc cgacagccag cccgacgcca acgctgaccc ctactgctac     2160
gcccacgccc acggcaagcc cgacgccgtc accgacggca gcctccggag cccgctgcac     2220
cgcgagttac caggtcaaca gcgattgggg caatggcttc acggtaacgg tggccgtgac     2280
aaattccgga tccgtcgcga ccaagacatg gacggtcagt tggacattcg gcggaaatca     2340
gacgattacc aattcgtgga atgcagcggt cacgcagaac ggtcagtcgg taacggctcg     2400
gaatatgagt tataacaacg tgattcagcc tggtcagaac accacgttcg gattccaggc     2460
gagctatacc ggaagcaacg cggcaccgac agtcgcctgc gcagcaagtt aatacgtcgg     2520
ggagccgacg ggagggtccg gaccgtcggt tccccggctt ccacctatgg agcgaaccca     2580
acaatccgga cggaactgca ggtaccagag aggaacgaca cgaatgcccg ccatctcaaa     2640
acggctgcga gccggcgtcc tcgccggggc ggtgagcatc gcagcctcca tcgtgccgct     2700
ggcgatgcag catcctgcca tcgccgcgac gcacgtcgac aatccctatg cgggagcgac     2760
cttcttcgtc aacccgtact gggcgcaaga agtacagagc gaacggcgaa ccagaccaat     2820
gccactctcg cagcgaaaat gcgcgtcgtt tccacatatt cgacggccgt ctggatggac     2880
cgcatcgctg cgatcaacgg cgtcaacggc ggacccggct tgacgacata tctgacgcc      2940 gccctctccc agcagcaggg aaccaccct gaagtcattg agattgtcat ctacgatctg      3000
```

-continued

| | |
|---|---:|
| ccgg | 3004 |

<210> SEQ ID NO 9
<211> LENGTH: 2220
<212> TYPE: DNA
<213> ORGANISM: Trichoderma reesei
<300> PUBLICATION INFORMATION:
<308> DATABASE ACCESSION NUMBER: Genbank E00389
<309> DATABASE ENTRY DATE: 1997-09-29
<310> PATENT DOCUMENT NUMBER: JP 1985149387-A1
<312> PUBLICATION DATE: 1985-08-06

<400> SEQUENCE: 9

| | |
|---|---:|
| aaggttagcc aagaacaata gccgataaag atagcctcat taaacggaat gagctagtag | 60 |
| gcaaagtcag cgaatgtgta tatataaagg ttcgaggtcc gtgcctccct catgctctcc | 120 |
| ccatctactc atcaactcag atcctccagg agacttgtac accatctttt gaggcacaga | 180 |
| aacccaatag tcaaccgcgg actggcatca tgtatcggaa gttggccgtc atcacggcct | 240 |
| tcttggccac agctcgtgct cagtcggcct gcactctcca atcggagact cacccgcctc | 300 |
| tgacatggca gaaatgctcg tctggtggca cttgcactca acagacaggc tccgtggtca | 360 |
| tcgacgccaa ctggcgctgg actcacgcta cgaacagcag cacgaactgc tacgatggca | 420 |
| acacttggag ctcgacccta tgtcctgaca acgagacctg cgcgaagaac tgctgtctgg | 480 |
| acggtgccgc ctacgcgtcc acgtacggag ttaccacgag cggtaacagc ctctccattg | 540 |
| gctttgtcac ccagtctgcg cagaagaacg ttggcgctcg cctttacctt atggcgagcg | 600 |
| acacgaccta ccaggaattc accctgcttg gcaacgagtt ctctttcgat gttgatgttt | 660 |
| cgcagctgcc gtaagtgact taccatgaac ccctgacgta tcttcttgtg ggctcccagc | 720 |
| tgactggcca atttaaggtg cggcttgaac ggagctctct acttcgtgtc catggacgcg | 780 |
| gatggtggcg tgagcaagta tcccaccaac aacgctggcg ccaagtacgg cacggggtac | 840 |
| tgtgacagcc agtgtccccg cgatctgaag ttcatcaatg gccaggccaa cgttgagggc | 900 |
| tgggagccgt catccaacaa cgcaaacacg ggcattggag acacggaag ctgctgctct | 960 |
| gagatggata tctgggaggc caactccatc tccgaggctc ttaccccca cccttgcacg | 1020 |
| actgtcggcc aggagatctg cgagggtgat gggtgcggcg gaacttactc cgataacaga | 1080 |
| tatgcggca cttgcgatcc cgatggctgc gactggaacc cataccgcct gggcaacacc | 1140 |
| agcttctacg gccctggctc aagctttacc ctcgatacca ccaagaaatt gaccgttgtc | 1200 |
| acccagttcg agacgtcggg tgccatcaac cgatactatg tccagaatgg cgtcacttc | 1260 |
| cagcagccca cgccgagct tggtagttac tctggcaacg agctcaacga tgattactgc | 1320 |
| acagctgagg agacagaatt cggcggatct ctttctcaga caagggcggc ctgactcagt | 1380 |
| tcaagaaggc tacctctggc ggcatggttc tggtcatgag tctgtgggat gatgtgagtt | 1440 |
| tgatggacaa acatgcgcgt tgacaaagag tcaagcagct gactgagatg ttacagtact | 1500 |
| acgccaacat gctgtggctg actccacct acccgacaaa cgagacctcc tccacacccg | 1560 |
| gtgccgtgcg cggaagctgc tccaccagct ccggtgtccc tgctcaggtc gaatctcagt | 1620 |
| ctcccaacgc caaggtcacc ttctccaaca tcaagttcgg acccattggc agcaccggca | 1680 |
| acccctagcgg cggcaaccct cccggcgaa accgtgcac caccaccacc cgccgcccag | 1740 |
| ccactaccac tggaagctct cccggaccta cccagtctca ctacggccag tgcggcggta | 1800 |
| ttggctacag cggccccacg gtctgcgcca gcggcacaac ttgccaggtc ctgaacccttt | 1860 |
| actactctca gtgcctgtaa agctccgtgc gaaagcctga cgcaccggta gattcttggt | 1920 |

-continued

```
gagcccgtat catgacggcg gcgggagcta catggccccg ggtgatttat tttttttgta      1980
tctacttctg acccttttca aatatacggt caactcatct ttcactggag atgcggcctg      2040
cttggtattg cgatgttgtc agcttggcaa attgtggctt tcgaaaacac aaaacgattc      2100
cttagtagcc atgcatttta agataacgga atagaagaaa gaggaaatta aaaaaaaaa      2160 aaaaacaaac atcccgttca taacccgtag aatcgccgct cttcgtgtat cccagtacca      2220
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Nar E1 PCR
    Primer

<400> SEQUENCE: 10
cggggcgccg gcggcggcta t                                                21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Sac E1 PCR
    Primer

<400> SEQUENCE: 11
ccgagctctt aacttgctgc                                                  20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Sac E1cd
    PCR Primer

<400> SEQUENCE: 12
tggagctcta gacaggatcg aaaat                                            25

<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: VSP leader
    coding sequence

<400> SEQUENCE: 13
tctagagtcg accatgaagt tgtttgtttt ctttgttgct gcagtagttt tggtagcatg      60
gccatgccat ggcgcc                                                      76

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: CBH2-2 PCR
    Primer

<400> SEQUENCE: 14
gctctagatg tatcggaagt tggc                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: CBH3-1 PCR Primer

<400> SEQUENCE: 15
cccccgggtt acaggcactg agag                                              24

<210> SEQ ID NO 16
<211> LENGTH: 2199
<212> TYPE: DNA
<213> ORGANISM: Cellulomonas fimi
<300> PUBLICATION INFORMATION:
<303> JOURNAL: Gene
<304> VOLUME: 44
<306> PAGES: 315-342
<307> DATE: 1986
<308> DATABASE ACCESSION NUMBER: Genbank M15823
<309> DATABASE ENTRY DATE: 1993-06-04

<400> SEQUENCE: 16

| | |
|---|---|
| ggatccggac ggtgggcgtc gtggccgaca ccgacgcgct ggagacgacc ttcgcggacg | 60 |
| tcgcggacct cgcgcggcag tgccggttcg gcgactgccg gcacgagcgg gagccgggt | 120 |
| gcgcggtgcg ggcggccgtc gagtcgggcg acctgccggc ccggcggctg gactcgtggc | 180 |
| ggcgcctgga gcgcgaggcg gcctaccagg cacggcgcag cgacggcggc tggccgcgga | 240 |
| ggagcgcgca cgctggaaga agatcaccaa ggagtaccag cggggatgc gcgggccggg | 300 |
| gcgtccgcgg agctgacggg cccgggaggc ccgcagccgg cggtggggga gtccgctcgg | 360 |
| cgccagcggg tgtcgaagcg acgggtcgaa gcgcgccaac gtcgcccgat ccggaactga | 420 |
| agcgattagg aaatcctcat ccgctcgcgc cgtggggcat tcgtcgggtt cctcgtcgg | 480 |
| gacccgcacg agcgtgccac gaggcccgaa cccaggggagc tccttgatgt ccaccccgcag | 540 |
| aaccgccgca gcgctgctgg cggccgcggc cgtcgccgtc ggcggtctga ccgccctcac | 600 |
| caccaccgcc gcgcaggcgg ctcccggctg ccgcgtcgac tacgccgtca ccaaccagtg | 660 |
| gcccggcggc ttcggcgcca acgtcacgat caccaacctc ggcgaccccg tctcgtcgtg | 720 |
| gaagctcgac tggacctaca ccgcaggcca gcggatccag cagctgtgga acggcaccgc | 780 |
| gtcgaccaac ggcggccagg tctccgtcac cagcctgccc tggaacggca gcatcccgac | 840 |
| cggcggcacg cgtcgttcg ggttcaacgg ctcgtgggcc gggtccaacc cgacgccggc | 900 |
| gtcgttctcg ctcaacggca ccacctgcac gggcaccgtg ccgacgacca gccccacgcc | 960 |
| gaccccgacg ccgacgaccc ccacgccgac gccgaccccg accccaccc ccacgccgac | 1020 |
| ggtcacgccg cagccgacca gcggcttcta cgtcgacccg acgacgcagg gctaccgcgc | 1080 |
| gtggcaggcc gcgtccggca cggacaaggc gctgctcgag aagatcgcgc tcaccccgca | 1140 |
| ggcgtactgg gtcggcaact gggccgacgc gtcgcacgcg caggccgagg tcgccgacta | 1200 |
| caccggccgc gccgtcgcgg ccgggaagac gccgatgctc gtcgtctacg cgatcccggg | 1260 |
| ccgcgactgc ggctcgcact ccggcggtgg tgtgtccgag tccgagtacg cgcgctgggt | 1320 |
| cgacaccgtc gcgcagggca tcaagggcaa cccgatcgtg atcctcgagc ccgacgcgct | 1380 |
| cgcgcagctc ggcgactgct ccggccaggg tgaccgcgtc ggcttcctca agtacgccgc | 1440 |
| caagtcgctc acccctcaagg gcgcgcgcgt ctacatcgac gcgggccacg cgaagtggct | 1500 |
| gtcggtcgac acgccggtga accgcctcaa ccaggtcggc ttcgagtacg cggtgggctt | 1560 |

```
cgcgctcaac acgtcgaact accagacgac ggcggacagc aaggcgtacg gccagcagat    1620
ctcgcagcgg ctgggcggca agaagttcgt catcgacacc tcgcgcaacg gcaacggctc    1680
gaacggcgag tggtgcaacc cgcgcggccg cgcgctcggc gaacgccggg tcgcggtgaa    1740
cgacggctcc ggcctggacg cgctcctgtg ggtcaagctg cccggcgagt ccgacggcgc    1800
gtgcaacggc ggcccggccg ccggccagtg gtggcaggag atcgccctgg agatggcgcg    1860
caacgccagg tggtgagctg agacctcgcc cacgacgagc ccgcggacgg cgcacgtgcg    1920
tccgcgggct cgtccgtccg gccgcgggcg cccggacgtc ggggcggcgg ggacaatggg    1980
gcggtggcag ggcagacgac ggaccgcacc cgacgacgga cgcgccgcgc tcgacgtgtg    2040
gcgcgccgac cccgcaggcg tgccgacccc ggcgcggcgg accgcggtcc ggttcacgct    2100
cgaggagctc gccgacgtgg cccccggcaa cgcggtcgag gtgcgcgtcc cgccggacgg    2160
cggccgtgca ggccgtgcag ggcccgcggc acacccggg                           2199
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: cenApst PCR
      Primer

<400> SEQUENCE: 17

```
ggctgcaggc ggctgccgcg tcgac                                             25
```

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: cemAsac PCR
      Primer

<400> SEQUENCE: 18

```
ccgagctctc accacctggc gtt                                               23
```

<210> SEQ ID NO 19
<211> LENGTH: 82
<212> TYPE: DNA
<213> ORGANISM: Artificial Sequence
<220> FEATURE:
<223> OTHER INFORMATION: Description of Artificial Sequence: VSP leader
      coding sequence

<400> SEQUENCE: 19

```
tctagagtcg accatgaagt tgtttgtttt ctttgttgca gcagtagttt tggtagcttg      60
gccttgccac ggcgctgcag tc                                                82
```

<210> SEQ ID NO 20
<211> LENGTH: 2286
<212> TYPE: DNA
<213> ORGANISM: Clostridium thermocellum
<300> PUBLICATION INFORMATION:
<303> JOURNAL: Nucleic Acids Res.
<304> VOLUME: 14
<305> ISSUE: 21
<306> PAGES: 8605-8613
<307> DATE: 1986
<308> DATABASE ACCESSION NUMBER: Genbank X04584
<309> DATABASE ENTRY DATE: 1999-02-10

<400> SEQUENCE: 20

-continued

```
aaactaaaac tcctatccaa tactttagtt cagttccagc atacgtctgt attcaaaatg      60
cctgtattta taactgcatt tataatacct gaagcaaata ataattaaac ttgtggaaga     120
aaggaggttg caacaggttt taaattatct taattcaggt attttacaat ttttaataaa     180
aaggggata aaggtaaaaa atgagtagaa tgaccttgaa aagcagcatg aaaaaacgtg      240
tgttatcttt gctcattgct gtagtgtttc taagcttgac cggagtattt ccttcgggat     300
tgattgagac caaagtgtca gctgcaaaaa taacggagaa ttatcaattt gattcacgaa     360
tccgttttaaa ctcaataggt tttataccga accacagcaa aaaggcgact atagctgcaa    420
attgttcaac cttttatgtt gttaaagaag acggaacaat agtgtatacc ggaacggcaa     480
cttcaatgtt tgacaatgat acaaaagaaa ctgtttatat tgctgatttt tcatctgtta     540
atgaagaagg aacgtactat cttgccgtgc cgggagtagg aaaaagcgta aactttaaaa     600
ttgcaatgaa tgtatatgag gatgctttta aaacagcaat gctgggaatg tatttgctgc     660
gctgcggcac cagtgtgtcg gccacataca acggaataca ctattcccat ggaccgtgcc     720
atactaatga tgcatatctt gattatataa acggacagca tactaaaaaa gacagtacaa     780
aaggctggca tgatgcgggc gactacaaca aatatgtggt aaacgccggc ataaccgttg     840
gttcaatgtt cctggcgtgg gagcatttta agaccagtt ggagcctgtg cattggaga      900
ttcccgaaaa gaacaattca ataccggatt tcttgatga attaaaatat gagatagact     960
ggattcttac catgcaatac cctgacggga gcggaagggt ggctcataaa gtttcgacaa    1020
ggaactttgg cggcttttatc atgcctgaga acgaacacga cgaaagattt ttcgtgccct   1080
ggagcagtgc cgcaacggca gactttgttg ccatgacggc catggctgca agaatattca    1140
ggccttatga tcctcaatat gctgaaaaat gtataaatgc ggcaaaagta agctatgagt    1200
ttttgaagaa caatcctgcg aatgttttttg caaaccagag tggattctca acaggagaat   1260
atgccactgt cagtgatgca gatgacagat tgtgggcggc ggctgaaatg tgggagaccc    1320
tgggagatga agaataccctt agagattttg aaaacagggc ggcgcaattc tcgaaaaaaa  1380
tagaagccga ttttgactgg gataatgttg caaacttagg tatgtttaca tatctttttgt  1440
cagaaagacc gggcaagaat cctgctttgg tgcagtcaat aaaggatagt ctcctttcca   1500
ctgcggattc aattgtgagg accagccaaa accatggcta tggcagaacc cttggtacaa   1560
catattactg gggatgcaac ggcacggttg taagacagac tatgatactt caggttgcga   1620
acaagatttc acccaacaat gattatgtaa atgctgctct cgatgcgatt tcacatgtat   1680
ttggaagaaa ctattacaac aggtcttatg taacaggcct tggtataaat cctcctatga   1740
atcctcatga cagacgttca ggggctgacg aatatggga gccgtggccc ggttaccttg    1800
taggaggagg atggcccgga ccgaaggatt gggtggatat tcaggacagt tatcagacca   1860
atgaaattgc tataaactgg aatgcggcat tgatttatgc ccttgccgga tttgtcaact    1920
ataattctcc tcaaaatgaa gtactgtacg gagatgtgaa tgatgacgga aaagtaaact   1980
ccactgactt gactttgtta aaaagatatg ttcttaaagc cgtctcaact ctcccttctt    2040
ccaaagctga aaagaacgca gatgtaaatc gtgacggaag agttaattcc agtgatgtca   2100
caatactttc aagatatttg ataagggtaa tcgagaaatt accaatataa attctgataa    2160
atattgataa acactaatat ataagtgttt aatcggtaaa agagccctgt ggcaaaaact    2220
gccgcaggct gttttttatca attccggcgc agacgaaaat agcagacgta aatattaatt    2280
actgaa                                                                2286
```

```
<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: celDpst PCR
      Primer

<400> SEQUENCE: 21
agctgcagaa ataacgg                                                  17

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: celDsac PCR
      Primer

<400> SEQUENCE: 22
ccgagctctt atattggtaa tttctc                                        26

<210> SEQ ID NO 23
<211> LENGTH: 4578
<212> TYPE: DNA
<213> ORGANISM: Clostridium cellulovorans
<300> PUBLICATION INFORMATION:
<303> JOURNAL: Gene
<304> VOLUME: 211
<305> ISSUE: 1
<306> PAGES: 39-47
<307> DATE: 1998
<308> DATABASE ACCESSION NUMBER: Genbank U34793
<309> DATABASE ENTRY DATE: 1999-03-09

<400> SEQUENCE: 23
taatatataa ataatattta aaatcaataa atcaatcggg gaaaatttaa aaaaagagag     60
ggataatcaa tgagaaaaag attaaataag atcgttgctg ttgctttaac tgcaacaact    120
atatcatcag tagcagctac tgttaataca gctcaagttt cagctgcacc agtagtgcca    180
aataatgagt atgttcaaca ctttaaggat atgtacgcta agatccataa tgcaaacaat    240
ggatacttca gtgatgaagg aataccttat cacgcagttg aaacattaat ggttgaagca    300
ccagactatg gtcatgaaac tacaagtgaa gcttgggatg taactgaaaa gtacataatt    360
ccaggtgaga ctgatcaacc aagcgcaagt atgagcaatt atgatccaaa taagccagct    420
acatatgcag ctgaacatcc agatccaagc atgtacccat ctcaattaca atttggtgct    480
gctgtaggta aggatccatt atacaatgaa ttaaaatcta cttatggaac tagccaagta    540
tatggtatgc attggttact agatgttgat aactggtatg gttttggtgg tgcaacaagc    600
acaagcccag tatacatcaa cactttccaa agaggtgttc aagaatcttg ttgggaaact    660
gtgccacaac catgtaaaga cgaaatgaag tacggtggaa gaaacggttt cttagatcta    720
ttcactggtg attcacaata cgcaactcaa tttaaatata ctaacgctcc agacgcagat    780
gctcgtgcag ttcaagctac ttactatgca caattagctg ctaaagaatg gggagtagac    840
atcagctcat atgtagcaaa atctactaag atgggtgact tcttaagata ttcattcttt    900
gataaatact ttagaaaagt tggaaattca acacaagcag gaactggata tgattcagct    960
caatacctat taaactggta ctatgcttgg ggtggtggaa tcagctcaaa ctggtcttgg   1020
agaattggat caagccataa ccatttcgga taccaaaacc caatggcagc atggatatta   1080
tcaaatacat ctgactttaa accaaagtca ccaaatgctg ctacagattg gataacagt    1140
```

-continued

```
ttaaagagac aaatagaatt ctatcaatgg ttacaatctg ctgaaggtgg tatcgctgga    1200
ggagctagta actcaaatgg aggaagctat caagcatggc cagcaggtac tcgaacattc    1260
tacggaatgg gatatactcc tcacccagta tacgaagatc caggtagtaa cgaatggttt    1320
ggtatgcaag catggtcaat gcaacgtgtg gctgaatact actacagttc aaaagatcca    1380
gcagctaaat cattacttga taaatgggct aaatggcttt gtgcaaatgt tcaattcgat    1440
gatgcagcta agaaatttaa gattcctgct aaattagtat ggactggaca accagatact    1500
tggactggat catatacagg aaattcaaat cttcatgtta aagttgaagc ttatggagaa    1560
gatcttggag tagcaggttc actttctaat gcattatcat attatgcaaa agctcttgaa    1620
tctagcacag atgctgcaga taaagtagca tataacactg caaagaaac ttctagaaag     1680 atacttgatt acttatggc aagctaccaa gatgataagg gtatagcagt tactgaaaca      1740
agaaatgatt tcaaacgttt caatcaatct gtatatattc catcaggttg gacaggaaaa    1800
atgcctaatg gagatgtaat ccaaagtgga gctactttct taagcatacg ttcaaaatac    1860
aaacaagatc catcatggcc aaatgttgaa gctgctttag caaatggtac tggtgttgat    1920 atgcatacc acagattctg gggtcaaagt gatatcgcta tagcatttgg aacatacggt      1980
acattattca cagaccctac tccaggatta aaaggtgatg ttaactctga tgctaaagta    2040
aatgctatag atttagctat attaaagaaa tacatcttag attcaacaac taaaattaac    2100
actgctaatt ctgatatgaa cggtgatgga aaagttaatg caatggattt agctttatta    2160
aagaaagcac ttctgcttaa gattaaataa ctttagatcg aaattgtaag gttatttaag    2220
gctggacaat atcaagtata ttgtccagct actttaaaaa atattgggaa acactgtgta    2280
aggtaaactt aaaccatgga tatgaaatat agtaagatta tgccattgc tatggcaaac     2340 ttaaaataaa tatattagag cataaacatg aaatttaagt aaaaggcgaa taaataattc    2400
cctaatcaaa aaaattaagg ggtggaacta gtgtttaaca tatctaagaa aaaagcgcaa    2460
gctcttcttt tatcaggaat cttgggtgca acttcattta caccagctgt attggtaaaa    2520
ggtgaaacaa cagcgactcc aacattcaat tatggagaag cattacaaaa gtcaataatg    2580
ttttatgaat ccaacgttc tggaaagtta ccaacggata ttcgtagtaa ttggcgtggt      2640
gattctggaa caaagatgg ctctgatgta ggagttgatt taactggtgg atggtatgat      2700
gctggagacc acgttaaatt taatctgcca atgtcttata ctgtggcaat gcttgcatgg    2760
tcattaagtg aagacaaagc agcttacgaa aaaagcggcc aattagatta ccttgttaag    2820
gaaataaaat gggctacaga ttatctaatg aagtgccata cggcaccaaa tgaatactat    2880
tatcaagttg gtgatggtgg agctgatcac aaatggtggg gacctgcaga agtaatgcag    2940
atggcaagac cggcttataa agtagatttg caaaaaccag gatcatcagt tgtcgctgaa    3000
acagcagcag cattagcttc tacagctttt gcattaaaag acatagataa agcgtattca    3060
gaacaatgta ttcagcatgc aaaagaactt tataactttg ctgatacaac aaagagtgat    3120 gctggtttata cagcagcaaa tacatattac aattcatgga gtggatacta tgatgaatta    3180
tcatgggctg cagcatggct ttacatggca acaaatgatg catcatatct agaaaaagcg    3240
gaatcatatg ttccattttg gaaggttgaa cagcaaacaa ccactatagc atatagatgg    3300
gcgcattgtt gggatgatgt acatttcgga gctcaattac tccttgccag attaacagga    3360
aaatcaatat acaagaatc agttgaaaga aaccttgatt attggacaac tggttatgat    3420
ggaaataaaa taagtacac tccaaaaggt ttagcttgga tggattcttg gggctcatta     3480
agatatgcaa ctacaacggc attccttgcc gatgtttatg caagctcaga tgtttgttct    3540
```

-continued

```
atttctaagg tagatacata taagaattttt gctaagagtc aagctgatta tgctttagga    3600
agtactggaa gaagttttgt ggtaggattt ggtgaaaatg ctccaaagaa accacatcat    3660
agaactgccc atagttcatg gtcagatcaa caagtaaatc caacagacca tagacatgtt    3720
ttatatggtg ctttagttgg aggaccagat gccagtgatg gttatactga tgctattgac    3780
aatttactta ataatgaggt ggcttgtgat tataatgcag gatttgtagg acttttagct    3840
agacaatatt ctaaatatgg cggagatcca atacctgatt ttaaagcgat agaaaagcca    3900
accaacgatg agttctttgt cgaagcagga gtaaattgta caggtccaaa ttttgtagaa    3960
attaaagctt tagttaataa tagaacagga tggccagcaa gaatgggaga taaactttca    4020
ttcaaatact tcataaatgt aagtgaattt gttaatgctg gttacagtgc agatgattta    4080
aaggttactg ttggttacaa tactggcgga actgtatcaa acctaatccc atgggataag    4140
gaaaataata tttattatgt aaatgttgat ttcacagggg taaagattta tccaggtgga    4200
caatcagatt ataaaaaaga aattcaattt agaatttcag gaattcaaaa tgttaatatt    4260
tgggataatt ctgatgactt ctcttatgag gggattacaa aaactccagg tgaaacacct    4320
gtgaaggtta caaacatccc agtttatgat aatggagtta aggtattcgg aaatgaacca    4380
ggaactacta gccacctgt tatagctggt gatgtaaaca ataatggtat cgtgaattca    4440 atggattag cgatgttaaa gaaatatata cttggatacg aagtagaaat gaataaagag    4500 gcttcgatt taaataaaga tggtaagatt aatgccattg atttcgctct tttaagaaa    4560 ctactttat cacagtag                                                   4578
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: exgSnar PCR
      Primer

<400> SEQUENCE: 24

```
cggggcgccg caccagtagt gcca                                              24
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: exgSsac PCR
      Primer

<400> SEQUENCE: 25

```
ccgagctctt atttaatctt aagc                                              24
```

<210> SEQ ID NO 26
<211> LENGTH: 5971
<212> TYPE: DNA
<213> ORGANISM: Thermobifida fusca
<300> PUBLICATION INFORMATION:

<400> SEQUENCE: 26

```
gcggccgcca ggtggggcgg ccgagtccga cggtggcgag gacttcgacc ccgtggtcgt     60
cagcgaagca tgcttcgctg acgttggcgg cggtgagcag gcctaccccg gtgccggtca    120
tcccgaagtg ggtggcgagt tcttcgaggt ggttgtccgg gtcggtccgc ggtagtcgc    180 cgtcgacttg ggcgttgatg acgtagtccc gtggtccgag gccgccgccg agcacgctgg    240
```

-continued

```
aggcggccat gcgccagccg gggccgcact gccagagcac tgcggcaagg gcgcggccgt      300
tgtcgcgccg ccagcgcagg tgcgcggtga ggagggtgcc gtcgccgatc gtctccgtgt      360
ccactccgct ctccagggtc ggttccgcgg ggccacttta acgagtccgc atcgggcggc      420
agcggggtca tgcttccatc tgggcgaatg ccacgcggag tactgcgagt ctcacgcttc      480
gtcccattgt cttttacgg agggtttaca cggcacatcc ggaacgttac cctcctactg       540
ggagcgctcc cgtgactcag gccacaggcc cccttcccgg ggcgagcccc caccaccccg      600
ggaaggccac tgcgacccct gagctcaatt catgggagcg ctcccatgcc agtgctcccg      660
gcagaaagga gagaaccgga acccggtacc gctggtttca ctgatccccc tgttttcacc      720
cggcatcgcc ccgacaccag cgatgccacc cccgcggcgg ctgcagtcca cacccggcac      780
gccgcacacc cctctcctgt gtgacacgcg gttccgaacg gccttgccgg ttctcggtat      840
gccgacgaac ggcacggctg ctccggaacc ggaagatccg gaggttattt ccaagcatga      900
gatcgttact gtctccccgg cgctggcgca cgctggcctc gggggcgctc gcagcggccc      960
tggccgccgc tgtactctcc cccggcgtcg cgcacgccgc cgtcgcctgc tcggtggact      1020
acgacgactc caacgactgg ggtagcgggt tcgtcgccga agtcaaggtg accaacgaag      1080
gcagcgaccc catccagaac tggcaagtag gctggacctt ccccggtaac cagcagatca      1140
ccaacggctg gaacggcgtg ttcagccaga gcggcgccaa cgtcaccgtc cgctacccgg      1200
actggaaccc caatatcgcc cccgagcca ccatctcctt cggcttccag ggcacctaca       1260
gcggctccaa cgacgcccg accagcttca ccgtcaacgg cgtcacctgc agcggatccc       1320
agcccgccaa cctgccgccc gatgtcaccc tgacatcccc ggccaacaac tcgaccttcc      1380
tggtcaacga cccgatcgag ctgaccgcgg tcgcctccga ccccgacggc tcgatcgacc      1440
gggtggaatt cgccgccgac aacaccgtca tcggcatcga caccacctcc ccctacagct      1500
tcacctggac ggacgctgcc gccggctcct actcggtgac cgcgatcgcc tacgacgacc      1560
agggagccag gaccgtctcc gctcccatcg ccatccgagt gctggaccgg gccgccgtca      1620
tcgcctcacc gcccaccgtc cgcgtgccgc agggcggcac cgccgacttc gaggtgcggc      1680
tgtccaacca gccctccggc aacgtcacgg tcaccgtggc gcgcacgtcg ggcagctccg      1740
acctgaccgt ctccagcggc tcccaactcc agttcacctc cagcaactgg aaccagccgc      1800
agaaggtgac catcgcctcc gctgacaacg gcggaaacct ggccgaggcg gtcttcaccg      1860
tcagcgcccc cggccacgac tcggccgagg tgacggtccg ggagatcgac ccgaacacca      1920
gctcctacga ccaggccttc ctggagcagt acgagaagat caaggacccc gccagcggct      1980
acttccgcga attcaacggg ctcctggtcc cctaccactc ggtggagacc atgatcgtcg      2040
aggctccgga ccacggccac cagaccacgt ccgaggcgtt cagctactac ctgtggctgg      2100
aggcgtacta cggccgggtc accggtgact ggaagccgct ccacgacgcc tgggagtcga      2160
tggagacctt catcatcccc ggcaccaagg accagccgac caactccgcc tacaacccga      2220
actccccggc gacctacatc cccgagcagc caacgctgac ggctacccg tcgcctctca       2280 tgaacaacgt cccggtgggt caagacccgc tcgcccagga gctgagctcc acctacggga      2340
ccaacgagat ctacgcatg cactggctgc tcgacgtgga caacgtctac ggcttcgggt       2400
tctgcggcga cggcaccgac gacgccccg cctacatcaa cacctaccag cgtggtgcgc       2460
gcgagtcggt gtgggagacc attccgcacc cgtcctgcga cgacttcacg cacggcggcc      2520
ccaacggcta cctggacctg ttcaccgacg accagaacta cgccaagcag tggcgctaca      2580
```

```
ccaacgcccc cgacgctgac gcgcgggccg tccaggtgat gttctgggcg cacgaatggg    2640
ccaaggagca gggcaaggag aacgagatcg cgggcctgat ggacaaggcg tccaagatgg    2700
gcgactacct ccggtacgcg atgttcgaca agtacttcaa gaagatcggc aactgcgtcg    2760
gcgccacctc ctgcccgggt ggccaaggca aggacagcgc gcactacctg ctgtcctggt    2820
actactcctg gggcggctcg ctcgacacct cctctgcgtg ggcgtggcgt atcggctcca    2880
gctcctcgca ccagggctac cagaacgtgc tcgctgccta cgcgctctcg caggtgcccg    2940
aactgcagcc tgactccccg accggtgtcc aggactgggc caccagcttc gaccgccagt    3000
tggagttcct ccagtggctg cagtccgctg aaggtggtat cgccggtggc gccaccaaca    3060
gctggaaggg aagctacgac accccgccga ccggcctgtc gcagttctac ggcatgtact    3120
acgactggca gccggtctgg aacgaccgc cgtccaacaa ctggttcggc ttccaggtct    3180
ggaacatgga gcgcgtcgcc cagctctact acgtgaccgg cgacgcccgg ccgaggcca    3240 tcctcgacaa gtgggtgccg tgggccatcc agcacaccga cgtggacgcc gacaacggcg    3300
gccagaactt ccaggtcccc tccgacctgg agtggtcggg ccagcctgac acctggaccg    3360
gcacctacac cggcaacccg aacctgcacg tccaggtcgt ctcctacagc caggacgtcg    3420
gtgtgaccgc cgctctggcc aagaccctga tgtactacgc gaagcgttcg ggcgacacca    3480
ccgccctcgc caccgcggag ggtctgctgg acgccctgct ggccaccgg acagcatcg    3540 gtatcgccac ccccgagcag ccgagctggg accgtctgga cgacccgtgg gacggctccg    3600
agggcctgta cgtgccgccg ggctggtcgg gcaccatgcc caacggtgac cgcatcgagc    3660
cgggcgcgac cttcctgtcc atccgctcgt tctacaagaa cgacccgctg tggccgcagg    3720
tcgaggcaca cctgaacgac ccgcagaacg tcccggcgcc gatcgtggag cgccaccgct    3780
tctgggctca ggtggaaatc gcgaccgcgt tcgcagccca cgacgaactg ttcggggccg    3840
gagctccctg atcctgaaca gtccgtctcc tgaccggcgg tccgtggcgg cgtagtgctc    3900
ccccgccgcg gaccgcccctc caccaccccc ctggggccgt ccggcgcacc aacaccggac    3960
ggccccagac tcctttcacg gcctgctact cggcccgacg ccccgcccta tccagcccga    4020
tcaaccaggt cagcgtagtc cgggtgccgc tcgagccacg ccttgacata ggggcagacc    4080
gcacgcaccc gcagcccgcg ggcccgcaca tcatccaacg cctcccgcac cagccggctg    4140
cccatcccct tccccctggaa agagccgtcc acccgagtgt ggaagaagac cacccgatca    4200
ccggcaacag gctggtattc cgtgaaaccg gcgatttcct ccccggcacg gatctcgtac    4260
cggtgctgtg ccggattgtc gatcaccgtg acatccatgc cgttcccctc ccgttcccca    4320
ggcggcggcg catctctcat ccggcggcct gcccaggact gtcctcttcc ccaggacagc    4380
ctgagcacgc gcccgcacgg cgaacccag ccacagccct agcatggtga acggccacgg    4440
tcgcagggcg accacgacac cgaggaggag tgatgggcga cggcggcaca gtacgccacc    4500
cttccgtacg tgccgtatca ccggcagcgt ggacgagcg ggtacgcgtc ctgcgggcag    4560
gcggcctcgt agctttcccc accgaaaccg tctacggcct aggcgcggac gccgcgaacc    4620
cggccgcggt agcgcgcatt ttcgccgcca aaggccgtcc cgctgaccac ccctgatcg    4680 tgcacgtcgc ttccgcggag agcgcgcgcg actgggctgc tacctttcct cctctcgccc    4740
gcacgctggc ggacgcgttc tggcccggcc cgctgaccct catcctcccc cgctccgccc    4800
aagtgccgga cgcagtgacc ggtggacgcg ccacggtagg gctgcgggtc cccgaccagc    4860
cggtcgcgct cgcactcctg gaacgcttcg gcggcggaat cgccgcacct tccgcgaacc    4920
ggttcggccg agtgagcccg accacggccg cgcacgttgc cgctgacctc ggggaccggg    4980
```

```
tcgacctggt gttggacggc ggaccgtgca cggtcggcgt ggaatcgacg atcgtcgaag    5040
tggccgacgg ccggctcacc gtgctccgca ccggaggcat caccccccgac gaccttgccg   5100 cggtcaccgg agcccccgtc gacaccaccc ccaccggacc ggcccgggca cccggcatgc    5160
tcgccgccca ctacgcaccc gccgcacggg tcgtgctagc cgaagcagca gaagccgcgg    5220
acacggtcgc ccagtgggtg gagaaaggac accgggtggc tgtgctggcg agaccgcta    5280 ccgtgcccga aaacctgccg gaaggcgtgg tggtgctacc gtcccctgct tcggctcggg    5340
actatgcccg cgtgctgtac cagcggctgc gggacgtgga cgcggcggga gccgacgtgg    5400
tcgtcgcgat ccccccccgaa cccgcgggga tcggcttggc ggtacgggac cggctgctgc    5460
gcgcatcccg ggcgcactga cctctccccc tggggcaagg gatttttccg catagacgag    5520
cccgtttccg ggatctcttt ctgtggagac agaaagagag caccgacacc agggagggcc    5580
gatgaaagct caagccggag accggatcgt tgtggaacgc ccccgcgatg acctgcccgc    5640
gcgcaaaggc gtcgtgctca agtgcaggg gacaacggg ggcccgccct actgggtgcg    5700
gtgggaggac gaaggccggg aaaccctcgt ctacccggga ccggacgccc gtatcgagcc    5760
ccgccacccc gtcccccaag cccgccagga gcatacggag gcccgtcaac cgcagccggg    5820
acagtccctg aaacggatac agatcgacgt cgcagtgtcg gaggtgcacg agaacggctc    5880
cgtgcgcacc ctcgccgaag cgcaactgcc gtccaccaag tggaacctgc gcggccacgg    5940
agaagcacgc aagcatccca ccgacgccga t                                   5971
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: celFpst
     PCR Primer

<400> SEQUENCE: 27
acgctgcagt cgcctgctcg g                                              21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:  celFxma
     PCR Primer

<400> SEQUENCE: 28
cccccgggtc agggagctcc ggc                                            23

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: 2777 PCR
     Primer

<400> SEQUENCE: 29
ggccacctgg gcagg                                                     15

<210> SEQ ID NO 30
<211> LENGTH: 17
<212> TYPE: DNA
<213> ORGANISM: Artificial Sequence -continued

```
<220> FEATURE:
<223> OTHER INFORMATION: Description of Artificial Sequence:  M13-20 PCR
      Primer

<400> SEQUENCE: 30
gtaaaacgac ggccagt                                                        17

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: 3227 PCR
      Primer

<400> SEQUENCE: 31
gcgacgctcg ggccg                                                          15

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Reverse
      3227 PCR Primer

<400> SEQUENCE: 32
aacagctatg accatg                                                         16
```